US009575072B2

(12) United States Patent
Thadhani et al.

(10) Patent No.: US 9,575,072 B2
(45) Date of Patent: Feb. 21, 2017

(54) DIAGNOSTIC AND THERAPEUTIC USES OF GELSOLIN IN RENAL FAILURE

(75) Inventors: Ravi Thadhani, Boston, MA (US); Thomas P. Stossel, Belmont, MA (US); Po-Shun Lee, Brookline, MA (US); Ananth Karumanchi, Chestnut Hill, MA (US)

(73) Assignees: The Brigham and Women's Hospital, Inc., Boston, MA (US); Beth Israel Deaconess Medical Center, Inc., Boston, MA (US); The General Hospital Corporation, Boston, MA (US)

( * ) Notice: Subject to any disclaimer, the term of this patent is extended or adjusted under 35 U.S.C. 154(b) by 70 days.

(21) Appl. No.: 12/358,868

(22) Filed: Jan. 23, 2009

(65) Prior Publication Data

US 2009/0258830 A1  Oct. 15, 2009

Related U.S. Application Data

(60) Provisional application No. 61/023,789, filed on Jan. 25, 2008.

(51) Int. Cl.
*G01N 33/53* (2006.01)
*A61K 38/17* (2006.01)
*A61P 13/12* (2006.01)
*G01N 33/68* (2006.01)
*C12Q 1/68* (2006.01)
*C07K 14/47* (2006.01)

(52) U.S. Cl.
CPC ....... *G01N 33/6893* (2013.01); *A61K 38/1709* (2013.01); *C12Q 1/6883* (2013.01); *C12Q 1/689* (2013.01); *C12Q 2600/118* (2013.01); *C12Q 2600/158* (2013.01); *G01N 2800/347* (2013.01)

(58) Field of Classification Search
None
See application file for complete search history.

(56) References Cited

U.S. PATENT DOCUMENTS

| | | |
|---|---|---|
| 5,071,773 A | 12/1991 | Evans et al. |
| 5,260,224 A | 11/1993 | Stossel et al. |
| 5,407,821 A | 4/1995 | Breakefield et al. |
| 5,464,817 A | 11/1995 | Stossel et al. |
| 5,508,265 A | 4/1996 | Stossel et al. |
| 5,569,588 A | 10/1996 | Ashby et al. |
| 5,571,511 A | 11/1996 | Fischer |
| 5,580,265 A | 12/1996 | Koblitz et al. |
| 5,593,964 A | 1/1997 | Goldstein et al. |
| 5,648,465 A | 7/1997 | Margolis et al. |
| 5,656,589 A | 8/1997 | Stossel et al. |
| 5,691,160 A | 11/1997 | Janmey et al. |
| 5,744,303 A | 4/1998 | Iggo et al. |
| 5,750,353 A | 5/1998 | Kopin et al. |
| 5,783,662 A | 7/1998 | Janmey et al. |
| 5,804,427 A | 9/1998 | Davis et al. |
| 5,830,436 A | 11/1998 | Ghio et al. |
| 5,846,743 A | 12/1998 | Janmey et al. |
| 5,925,529 A | 7/1999 | Coughlin et al. |
| 6,040,147 A | 3/2000 | Ridker et al. |
| 6,271,353 B1 | 8/2001 | Nakamura et al. |
| 6,319,498 B1 | 11/2001 | Findeis et al. |
| 7,432,308 B2 | 10/2008 | Demeester et al. |
| 7,928,089 B2 | 4/2011 | Morton et al. |
| 8,198,094 B2 | 6/2012 | Stossel et al. |
| 8,440,622 B2 | 5/2013 | Stossel et al. |
| 9,316,639 B2 | 4/2016 | Stossel et al. |
| 9,408,891 B2 | 8/2016 | Janmey et al. |
| 2002/0103112 A1 | 8/2002 | Ferguson et al. |
| 2003/0083262 A1 | 5/2003 | Hannig et al. |
| 2004/0072261 A1 | 4/2004 | Kostanjevecki et al. |
| 2004/0141961 A1 | 7/2004 | Demeester et al. |
| 2006/0009386 A1 | 1/2006 | Stossel et al. |
| 2007/0087969 A1 | 4/2007 | Ferguson et al. |
| 2007/0238655 A1 | 10/2007 | Bucki et al. |
| 2007/0238668 A1 | 10/2007 | Janmey et al. |
| 2008/0051348 A1 | 2/2008 | Goldstein et al. |
| 2008/0125370 A1 | 5/2008 | Stossel et al. |
| 2008/0261260 A1 | 10/2008 | Stossel et al. |
| 2009/0053194 A1 | 2/2009 | Goldstein et al. |
| 2010/0021428 A1 | 1/2010 | Stossel et al. |
| 2010/0227807 A1 | 9/2010 | Stossel et al. |
| 2011/0144020 A1 | 6/2011 | Goldstein et al. |
| 2012/0208743 A1 | 8/2012 | Stossel et al. |
| 2013/0230455 A1 | 9/2013 | Stossel et al. |
| 2015/0191695 A1 | 7/2015 | Song et al. |
| 2016/0228505 A1 | 8/2016 | Stossel et al. |

FOREIGN PATENT DOCUMENTS

| | | |
|---|---|---|
| CA | 2 142 121 A | 3/1994 |
| JP | H05-506034 A | 9/1993 |
| JP | H08-500488 A | 1/1996 |

(Continued)

OTHER PUBLICATIONS

Lee et al (2009. J Am Soc Nephrol. 20: 1140-1148).*
Lee et al, 2010. Blood Purif. 29: 99-101).*
Mounzer et al, 1999. Am J Respir Crit Care med. 160: 1673-1681.*
Lee et al, 2006, Ann Surg. 243: 399-403.*
Supplemental European Search Report for EP 05750392.2 mailed Jan. 18, 2008.
Partial European Search Report for EP 10185573.2 mailed Apr. 1, 2011.
Invitation to Pay Additional Fees for PCT/US2005/016798 mailed Nov. 18, 2005.
International Search Report and Written Opinion for PCT/US2005/016798 mailed Jan. 20, 2006.
International Preliminary Report on Patentability for PCT/US2005/016798 mailed Nov. 23, 2006.
Extended European Search Report for EP 07753226.5 mailed Feb. 17, 2009.
International Search Report and Written Opinion for PCT/US2007/006581 mailed Aug. 11, 2008.
International Preliminary Report on Patentability for PCT/US2007/006581 mailed Sep. 25, 2008.
Extended European Search Report for EP 07753102.8 mailed Jun. 10, 2009.

(Continued)

*Primary Examiner* — Zachary Howard
(74) *Attorney, Agent, or Firm* — Wolf, Greenfield & Sacks, P.C.

(57) ABSTRACT

The invention is directed, in part, to the use of gelsolin to diagnose, monitor, and treat subjects with renal failure (e.g., chronic renal failure subjects on dialysis).

16 Claims, 7 Drawing Sheets

(56) References Cited

FOREIGN PATENT DOCUMENTS

| | | | |
|---|---|---|---|
| JP | 2003-511356 A | 3/2003 |
| JP | 2004-532386 | 10/2004 |
| JP | 2004-534841 A | 11/2004 |
| JP | 2004-536786 A | 12/2004 |
| JP | 2005-041881 A | 2/2005 |
| JP | 2005-525998 A | 9/2005 |
| JP | 2007-524101 A | 8/2007 |
| JP | 2007-537292 A | 12/2007 |
| WO | WO 91/15770 A1 | 10/1991 |
| WO | WO 91/17170 A1 | 11/1991 |
| WO | WO 94/04704 A1 | 3/1994 |
| WO | WO 94/22465 A1 | 10/1994 |
| WO | WO 95/09645 A1 | 4/1995 |
| WO | WO 98/04589 A2 | 2/1998 |
| WO | WO 00/55350 A1 | 9/2000 |
| WO | WO 02/059604 A2 | 8/2002 |
| WO | WO 02/070007 A1 | 9/2002 |
| WO | WO 03/006026 A1 | 1/2003 |
| WO | WO 03/020213 A2 | 3/2003 |
| WO | WO 03/088811 A2 | 10/2003 |
| WO | WO 2004/023973 A2 | 3/2004 |
| WO | WO 01/24828 A2 | 4/2004 |
| WO | WO 2004/035008 A2 | 4/2004 |
| WO | WO 2004/082617 A2 | 9/2004 |
| WO | WO 2005/046454 A2 | 5/2005 |
| WO | WO 2005/085859 A1 | 9/2005 |
| WO | WO 2005/112970 A2 | 12/2005 |
| WO | WO 2007/041245 A2 | 4/2007 |
| WO | WO 2007/106577 A2 | 9/2007 |
| WO | WO 2007/109056 A2 | 9/2007 |
| WO | WO 2009/094194 A2 | 7/2009 |
| WO | WO 2016/033187 A1 | 3/2016 |

OTHER PUBLICATIONS

International Search Report and Written Opinion for PCT/US2007/006451 mailed Sep. 25, 2007.
International Preliminary Report on Patentability for PCT/US2007/006451 mailed Sep. 25, 2008.
Supplemental European Search Report for EP 04810817.9 mailed Jun. 10, 2010.
Invitation to Pay Additional Fees for PCT/US2004/037763 mailed May 5, 2005.
International Search Report and Written Opinion for PCT/US2004/037763 mailed Aug. 31, 2005.
International Preliminary Report on Patentability for PCT/US2004/037763 mailed May 26, 2006.
Extended European Search Report for EP 09703176.9 mailed Jan. 17, 2011.
Invitation to Pay Additional Fees for PCT/US2009/000452 mailed Mar. 16, 2009.
International Search Report and Written Opinion for PCT/US2009/000452 mailed May 18, 2009.
International Preliminary Report on Patentability for PCT/US2009/000452 mailed Aug. 5, 2010.
Genbank Submission; NIH/NCBI, Accession No. 1211330A; Kwiatkowski et al.; Oct. 1, 1996. Last accessed Feb. 3, 2005 at http:ncbi.nlm.nih.gov/entrez/viewer.fcgi?db=protein&val=225304. 2 pages.
Genbank Submission; NIH/NCBI, Accession No. CAA28000; Kwiatkowski et al.; Mar. 21, 1995. Last accessed Feb. 3, 2005 at http:ncbi.nlm.nih.gov/entrez/viewer.fcgi?db=protein&val=736249. 2 pages.
Genbank Submission; NIH/NCBI, Accession No. X04412.1; Kwiatkowski et al.; Oct. 7, 2008.
[No Author Listed] "Risk". Dorlands Medical Dictionary. Merck Source. Last accessed on Jun. 29, 2009 available at www.mercksource.com/pp/us/cns/snc_hl_dorlands_split.jsp?pg=/ppdocs/us/common/dorlands/dorland/seven/000093452.html, 2009. 2 pages.

[No Author Listed] "Risk". Medical Dictionary. Last accessed on Jun. 29, 2009 available at www.medicaldictionaryweb.com/Rish-definition/2009. 1 page.
[No Author Listed] "Risk". Rogets II The New Thesaurus NY, Expanded Edition. Houghton Mifflin Company. New York 1988:843.
Adams et al., Fibrin mechanisms and functions in nervous system pathology. Mol Interv. Jun. 2004;4(3):163-76.
Aidinis et al., Cytoskeletal rearrangements in synovial fibroblasts as a novel pathophysiological determinant of modeled rheumatoid arthritis. PLoS Genet. Oct. 2005;1(4):e48. Epub Oct. 28, 2005 12 pages.
Angus et al., Epidemiology of sepsis: an update. Crit Care Med. Jul. 2001;29(7 Suppl):S109-16.
Bannerman et al., Increased levels of LPS-binding protein in bovine blood and milk following bacterial lipopolysaccharide challenge. J Dairy Sci. Oct. 2003;86(10):3128-37.
Barnard et al., Targeted deletion of gelsolin potentiates endotoxin-induced murine lung vascular leak. FASEB. 2004;18(4-5):A352. Abstract 233.8.
Becker et al., Pulmonary vascular permeability and ischemic injury in gelsolin-deficient mice. Am J Respir Cell Mol Biol. Apr. 2003;28(4):478-84.
Beddhu et al., Inflammation and inverse associations of body mass index and serum creatinine with mortality in hemodialysis patients. J Ren Nutr. Nov. 2007;17(6):372-80.
Berer et al., Are the serum levels of endotoxin-binding proteins reliable predictors of complications in the course of peritonitis? Eur J Clin Invest. Feb. 1990;20(1):66-71.
Berger et al, Evidence for endotoxin binding capacity of human Gc-globulin and transferrin. Clin Chim Acta. Mar. 30, 1987;163(3):289-99.
Beutler et al, Sepsis and evolution of the innate immune response. Crit Care Med. Jul. 2001;29(7 Suppl):S2-6; discussion S6-7.
Bochicchio et al., Reclassification of urinary tract infections in critically ill trauma patients: a time-dependent analysis. Surg Infect (Larchmt). 2003 Winter;4(4):379-85. Abstract only.
Bosshart et al., Endotoxin-neutralizing effects of histidine-rich peptides. FEBS Lett. Oct. 9, 2003;553(1-2):135-40.
Bowman et al., Cultured astrocytes express toll-like receptors for bacterial products. Glia. Sep. 2003;43(3):281-91.
Brandenburg et al., Physicochemical properties of bacterial glycopolymers in relation to bioactivity. Carbohydr Res. Nov. 14, 2003;338(23):2477-89.
Bsibsi et al., Broad expression of Toll-like receptors in the human central nervous system. J Neuropathol Exp Neurol. Nov. 2002;61(11):1013-21.
Bucki et al., Antibacterial activities of rhodamine B-conjugated gelsolin-derived peptides compared to those of the antimicrobial peptides cathelicidin LL37, magainin II, and melittin. Antimicrob Agents Chemother. May 2004;48(5):1526-33.
Bucki et al., Bacterial endotoxin as inhibitor of the enzymatic activity of human thrombin. Eur J Haematol. Jun. 2006;76(6):510-5. Epub Mar. 9, 2006.
Bucki et al., Extracellular gelsolin binds lipoteichoic acid and modulates cellular response to proinflammatory bacterial wall components. J Immunol. Oct. 1, 2008;181(7):4936-44.
Bucki et al., Inactivation of endotoxin by human plasma gelsolin. Biochemistry. Jul. 19, 2005;44(28):9590-7.
Candiano et al., Gelsolin secretion in interleukin-4-treated bronchial epithelia and in asthmatic airways. Am J Respir Crit Care Med. Nov. 1, 2005;172(9):1090-6. Epub Aug. 11, 2005.
Casas et al., Reconstituted high-density lipoprotein reduces LPS-stimulated TNF alpha. J Surg Res. Nov. 1995;59(5):544-52.
Chauhan et al., Binding of gelsolin, a secretory protein, to amyloid beta-protein. Biochem Biophys Res Commun. May 10, 1999;258(2):241-6.
Christofidou-Solomidou et al., Changes in plasma gelsolin concentration during acute oxidant lung injury in mice. Lung. 2002;180(2):91-104.
Christofidou-Solomidou et al., Recombinant plasma gelsolin diminishes the acute inflammatory response to hyperoxia in mice. J Investig Med. Jan. 2002;50(1):54-60.

(56) References Cited

OTHER PUBLICATIONS

Cirioni et al., Potential therapeutic role of histatin derivative P-113d in experimental rat models of Pseudomonas aeruginosa sepsis. J Infect Dis. Jul. 15, 2004;190(2):356-64. Epub Jun. 21, 2004.

Cohen et al., Therapeutic potential of plasma gelsolin administration in a rat model of sepsis. Cytokine. Jun. 2011;54(3):235-8. Epub Mar. 21, 2011.

Cunningham et al., Cell permeant polyphosphoinositide-binding peptides that block cell motility and actin assembly. J Biol Chem. Nov. 16, 2001;276(46):43390-9. Epub Aug. 30, 2001.

Dahl et al., Plasma concentration of Gc-globulin is associated with organ dysfunction and sepsis after injury. Crit Care Med. Jan. 2003;31(1):152-6.

Dahl et al., Plasma gelsolin is reduced in trauma patients. Shock. Aug. 1999;12(2):102-4.

Dahl et al., Serum Gc-globulin in the early course of multiple trauma. Crit Care Med. Feb. 1998;26(2):285-9.

Dinubile et al., Decreased gelsolin levels are associated with interstitial pneumonia after allogenic BMT. Blood. 1998;92(Suppl):683a. Abstract 2814.

Dinubile et al., Prognostic implications of declining plasma gelsolin levels after allogeneic stem cell transplantation. Blood. Dec. 15, 2002;100(13):4367-71. Epub Aug. 1, 2002.

Erridge et al., Structure and function of lipopolysaccharides. Microbes Infect. Jul. 2002;4(8):837-51.

Erukhimov et al., Actin-containing sera from patients with adult respiratory distress syndrome are toxic to sheep pulmonary endothelial cells. Am J Respir Crit Care Med. Jul. 2000;162(1):288-94.

Faure et al., Bacterial lipopolysaccharide activates NF-kappaB through toll-like receptor 4 (TLR-4) in cultured human dermal endothelial cells. Differential expression of TLR-4 and TLR-2 in endothelial cells. J Biol Chem. Apr. 14, 2000;275(15):11058-63.

Flanagan et al., The structure of divalent cation-induced aggregates of PIP2 and their alteration by gelsolin and tau. Biophys J. Sep. 1997;73(3):1440-7.

Fouque et al., A proposed nomenclature and diagnostic criteria for protein-energy wasting in acute and chronic kidney disease. Kidney Int. Feb. 2008;73(4):391-8. Epub Dec. 19, 2007.

Ginsburg, Role of lipoteichoic acid in infection and inflammation. Lancet Infect Dis. Mar. 2002;2(3):171-9.

Goetzl et al., Gelsolin binding and cellular presentation of lysophosphatidic acid. J Biol Chem. May 12, 2000;275(19):14573-8.

Goetzl, Pleiotypic mechanisms of cellular responses to biologically active lysophospholipids. Prostaglandins. Apr. 2001;64(1-4):11-20.

Goldschmidt-Clermont et al., Role of group-specific component (vitamin D binding protein) in clearance of actin from the circulation in the rabbit. J Clin Invest. May 1988;81(5):1519-27.

Güntert et al., Plasma gelsolin is decreased and correlates with rate of decline in Alzheimer's disease. J Alzheimers Dis. 2010;21(2):585-96. Abstract only.

Gutsmann et al., Dual role of lipopolysaccharide (LPS)-binding protein in neutralization of LPS and enhancement of LPS-induced activation of mononuclear cells. Infect Immun. Nov. 2001;69(11):6942-50.

Haddad et al., Angiopathic consequences of saturating the plasma scavenger system for actin. Proc Natl Acad Sci U S A. Feb. 1990;87(4):1381-5.

Harris et al., Lipoprotein-bound LPS induces cytokine tolerance in hepatocytes. J Endotoxin Res. 2003;9(1):45-50.

Hartung et al., Inflammatory mediators in demyelinating disorders of the CNS and PNS. J Neuroimmunol. Oct. 1992;40(2-3):197-210.

Hattar et al., Lipoteichoic acid (LTA) from *Staphylococcus aureus* stimulates human neutrophil cytokine release by a CD14-dependent, Toll-like-receptor-independent mechanism: Autocrine role of tumor necrosis factor-[alpha] in mediating LTA-induced interleukin-8 generation. Crit Care Med. Mar. 2006;34(3):835-41.

Hayter et al., Neutron scattering analysis of bacterial lipopolysaccharide phase structure. Changes at high pH. J Biol Chem. Apr. 15, 1987;262(11):5100-5.

Himmelfarb et al., The elephant in uremia: oxidant stress as a unifying concept of cardiovascular disease in uremia. Kidney Int. Nov. 2002;62(5):1524-38.

Hsueh et al., Hypertension, the endothelial cell, and the vascular complications of diabetes mellitus. Hypertension. Aug. 1992;20(2):253-63.

Huang et al, Temporal association between serum gelsolin levels and clinical events in a patient with severe falciparum malaria. Clin Infect Dis. May 1997;24(5):951-4.

Hummell et al., Bacterial lipoteichoic acid sensitizes host cells for destruction by autologous complement. J Clin Invest. May 1986;77(5):1533-8.

Hyde et al., Mortality and bacteriology of sepsis following cecal ligation and puncture in aged mice. Infect Immun. Mar. 1990;58(3):619-24.

Igarashi et al., Sphingosine-phosphate content in the plasma of platelet concentrates correlates with poor platelet increments after transfusion and with occurrences of transfusion reactions in patients. Am J Hematol. Mar. 1998;57(3):261-2.

Ito et al., Depression of plasma gelsolin level during acute liver injury. Gastroenterology. May 1992;102(5):1686-92.

Janmey et al., Capacity of human serum to depolymerize actin filaments. Blood. Aug. 1987;70(2):524-30.

Janmey et al., Deconstructing gelsolin: identifying sites that mimic or alter binding to actin and phosphoinositides. Chem Biol. Apr. 1998;5(4):R81-5.

Janmey et al., Functional comparison of villin and gelsolin. Effects of Ca2+, KCl, and polyphosphoinositides. J Biol Chem. Nov. 15, 1988;263(32):16738-43.

Janmey et al., Interactions of gelsolin and gelsolin-actin complexes with actin. Effects of calcium on actin nucleation, filament severing, and end blocking. Biochemistry. Jul. 2, 1985;24(14):3714-23.

Janmey et al., Modulation of gelsolin function by phosphatidylinositol 4,5-bisphosphate. Nature. Jan. 22-28, 1987;325(6102):362-4.

Janmey et al., Polyphosphoinositide micelles and polyphosphoinositide-containing vesicles dissociate endogenous gelsolin-actin complexes and promote actin assembly from the fast-growing end of actin filaments blocked by gelsolin. J Biol Chem. Sep. 5, 1987;262(25):12228-36.

Janmey, Phosphoinositide-binding peptides derived from the sequences of gelsolin and villin. J Biol Chem. Jun. 15, 1992;267(17):11818-23.

Jensen et al., Features of endothelial dysfunction in early diabetic nephropathy. Lancet. Mar. 4, 1989;1(8636):461-3.

Jordan et al., Gelsolin is depleted in post-shock mesenteric lymph. J Surg Res. Nov. 2007;143(1):130-5. doi: 10.1016/j.jss.2007.04.017.

Jorgensen et al., Peptidoglycan and lipoteichoic acid modify monocyte phenotype in human whole blood. Clin Diagn Lab Immunol. May 2001;8(3):515-21.

Kalantar-Zadeh et al., A malnutrition-inflammation score is correlated with morbidity and mortality in maintenance hemodialysis patients. Am J Kidney Dis. Dec. 2001;38(6):1251-63.

Kalantar-Zadeh et al., Effect of malnutrition-inflammation complex syndrome on EPO hyporesponsiveness in maintenance hemodialysis patients. Am J Kidney Dis. Oct. 2003;42(4):761-73.

Kawamura et al., Lipoteichoic acid-induced neutrophil adhesion via E-selectin to human umbilical vein endothelial cells (HUVECs). Biochem Biophys Res Commun. Dec. 26, 1995;217(3):1208-15.

Kaysen et al., Longitudinal and cross-sectional effects of C-reactive protein, equilibrated normalized protein catabolic rate, and serum bicarbonate on creatinine and albumin levels in dialysis patients. Am J Kidney Dis. Dec. 2003;42(6):1200-11.

Kent et al., A monoclonal antibody to alpha 4 integrin suppresses and reverses active experimental allergic encephalomyelitis. J Neuroimmunol. Apr. 1995;58(1):1-10.

(56) References Cited

OTHER PUBLICATIONS

Kouyama et al., Fluorimetry study of N-(1-pyrenyl)iodoacetamide-labelled F-actin. Local structural change of actin protomer both on polymerization and on binding of heavy meromyosin. Eur J Biochem. 1981;114(1):33-8.
Kulakowska et al., Gelsolin concentration in cerebrospinal fluid from patients with multiple sclerosis and other neurological disorders. Eur J Neurol. Jun. 2008;15(6):584-8.
Kulakowska et al., Hypogelsolinemia, a disorder of the extracellular actin scavenger system, in patients with multiple sclerosis. BMC Neurol. Nov. 1, 2010;10:107. 8 pages.
Kwiatkowski, Functions of gelsolin: motility, signaling, apoptosis, cancer. Curr Opin Cell Biol. Feb. 1999;11(1):103-8.
Kwiatkowski et al., Identification of critical functional and regulatory domains in gelsolin. J Cell Biol. May 1989;108(5):1717-26.
Kwiatkowski et al., Isolation and properties of two actin-binding domains in gelsolin. J Biol Chem. Dec. 5, 1985;260(28):15232-8.
Kwiatkowski et al., Muscle is the major source of plasma gelsolin. J Biol Chem. Jun. 15, 1988;263(17):8239-43.
Kwiatkowski et al., Plasma and cytoplasmic gelsolins are encoded by a single gene and contain a duplicated actin-binding domain. Nature. Oct. 2-8, 1986;323(6087):455-8.
Lazarus et al., Role of bioincompatibility in dialysis morbidity and mortality. Am J Kidney Dis. Dec. 1994;24(6):1019-32.
Lee et al., Plasma Gelsolin Depletion and Circulating Actin in Sepsis: A Pilot Study. PLoS One. 2008;3(11):e3712. doi:10.1371/journal.pone.0003712. 5 pages.
Lee et al., Plasma Gelsolin Is a Critical Pro-Survival Factor in Sepsis. American Thoracic Society. 2005. Last accessed Feb. 15, 2012 at http://www.mindcull.com/data/american-thoracic-society/ats-2005-american-thoracic-soci . . . Abstract only. 1 page.
Lee et al., Plasma gelsolin is a marker and therapeutic agent in animal sepsis. Crit Care Med. Mar. 2007;35(3):849-55.
Lee et al., Plasma Gelsolin Levels Predict the Outcomes of Critically Ill Patients in Surgical Intensive Care Unit. American Thoracic Society International Conference. Apr. 2004;167(7):A627. (ATS 2004—Orlando).
Lee et al., The extracellular actin-scavenger system and actin toxicity. N Engl J Med. May 14, 1992;326(20):1335-41.
Li et al., The critical micelle concentrations of lysophosphatidic acid and sphingosylphosphorylcholine. Chem Phys Lipids. Jul. 2004;130(2):197-201.
Liepina et al., Molecular dynamics study of a gelsolin-derived peptide binding to a lipid bilayer containing phosphatidylinositol 4,5-bisphosphate. Biopolymers. 2003;71(1):49-70.
Lind et al., Depression of gelsolin levels and detection of gelsolin-actin complexes in plasma of patients with acute lung injury. Am Rev Respir Dis. Aug. 1988;138(2):429-34.
Lind et al., Human plasma gelsolin binds to fibronectin. J Biol Chem. Nov. 10, 1984;259(20:13262-6.
Lind et al., Role of plasma gelsolin and the vitamin D-binding protein in clearing actin from the circulation. J Clin Invest. Sep. 1986;78(3):736-42.
Löfberg et al., Serum gelsolin and rhabdomyolysis. J Neurol Sci. May 7, 1998;157(2):187-90.
Masover et al., The effect of growth and urea concentration on ammonia production by a urea-hydrolysing mycoplasma (Ureaplasma urealyticum). J Gen Microbiol. Feb. 1977;98(2):587-93.
Mathison et al., Plasma lipopolysaccharide (LPS)-binding protein. A key component in macrophage recognition of gram-negative LPS. J Immunol. Jul. 1, 1992;149(1):200-6.
Matsumoto et al., Diagnosis of sepsis based on the host response. The Official Journal of Japanese Society of Laboratory Medicine. 1999;47(6):494-500. Japanese language reference.
Matsuoka et al., Novel therapeutic approach for the treatment of Alzheimer's disease by peripheral administration of agents with an affinity to beta-amyloid. J Neurosci. Jan. 1, 2003;23(1):29-33.

Maury, Homozygous familial amyloidosis, Finnish type: demonstration of glomerular gelsolin-derived amyloid and non-amyloid tubular gelsolin. Clin Nephrol. Jul. 1993;40(1):53-6. Abstract only.
McIntyre et al., Patients receiving maintenance dialysis have more severe functionally significant skeletal muscle wasting than patients with dialysis-independent chronic kidney disease. Nephrol Dial Transplant. Aug. 2006;21(8):2210-6. Epub Feb. 27, 2006.
Meerschaert et al., Gelsolin and functionally similar actin-binding proteins are regulated by lysophosphatidic acid. EMBO J. Oct. 15, 1998;17(20):5923-32.
Mertsola et al., Release of endotoxin after antibiotic treatment of Gram-negative bacterial meningitis. Pediatr Infect Dis J. Dec. 1989;8(12):904-6.
Mezzano et al., Endothelial cell markers in chronic uremia: relationship with hemostatic defects and severity of renal failure. Thromb Res. Dec. 15, 1997;88(6):465-72.
Mezzano et al., Inflammation, not hyperhomocysteinemia, is related to oxidative stress and hemostatic and endothelial dysfunction in uremia. Kidney Int. Nov. 2001;60(5):1844-50.
Mintzer et al., Lysophosphatidic acid and lipopolysaccharide bind to the PIP2-binding domain of gelsolin. Biochim Biophys Acta. Jan. 2006;1758(1):85-9. Epub Jan. 18, 2006.
Mitch et al., Mechanisms of muscle wasting. The role of the ubiquitin-proteasome pathway. N. Engl J Med. Dec. 19, 1996;335(25):1897-905.
Morgan, Risk factors for infection in the trauma patient. J Natl Med Assoc. Dec. 1992;84(12):1019-23.
Moss, Epidemiology of sepsis: race, sex, and chronic alcohol abuse. Clin Infect Dis. Nov. 15, 2005;41 Suppl 7:S490-7.
Myers et al., Collagen-induced arthritis, an animal model of autoimmunity. Life Sci. 1997;61(19):1861-78.
Nandakumar et al., Efficient promotion of collagen antibody induced arthritis (CAIA) using four monoclonal antibodies specific for the major epitopes recognized in both collagen induced arthritis and rheumatoid arthritis. J Immunol Methods. Sep. 2005;304(1-2):126-36.
Ni et al., The ubiquitin-proteasome pathway mediates gelsolin protein downregulation in pancreatic cancer. Mol Med. Sep.-Oct. 2008;14(9-10):582-9.
Nollet et al., Protection of just weaned pigs against infection with F18+ *Escherichia coli* by non-immune plasma powder. Vet Microbiol. Feb. 23, 1999;65(1):37-45.
Nugent et al., Sphingosine-l-phosphate: characterization of its inhibition of platelet aggregation. Platelets. Jun. 2000;11(4):226-32.
Osborn et al., Decreased levels of the gelsolin plasma isoform in patients with rheumatoid arthritis. Arthritis Res Ther. 2008;10(5):R117. Epub Sep. 27, 2008. 9 pages.
Osborn et al., Modifications of cellular responses to lysophosphatidic acid and platelet-activating factor by plasma gelsolin. Am J Physiol Cell Physiol. Apr. 2007;292(4):C1323-30. Epub Nov. 29, 2006.
Otero-Antón et al. Cecal ligation and puncture as a model of sepsis in the rat: influence of the puncture size on mortality, bacteremia, endotoxemia and tumor necrosis factor alpha levels. Eur Surg Res. 2001;33(2):77-9.
Overhaus et al., Mechanisms of polymicrobial sepsis-induced ileus. Am J Physiol Gastrointest Liver Physiol. Sep. 2004;287(3):G685-94.
Overland et al., Lipoteichoic acid is a potent inducer of cytokine production in rat and human Kupffer cells in vitro. Surg Infect (Larchmt). 2003 Summer;4(2):181-91.
Owen et al., The urea reduction ratio and serum albumin concentration as predictors of mortality in patients undergoing hemodialysis. N Engl J Med. Sep. 30, 1993;329(14):1001-6.
Riedermann et al., The enigma of sepsis. J Clin Invest. Aug. 2003;112(4):460-7.
Rogers et al., Relationship of Gelsolin Levels to Outcomes in Critically Ill Patients. J Surg Res. 2002;107(2):305-6.
Rothenbach et al., Recombinant plasma gelsolin infusion attenuates burn-induced pulmonary microvascular dysfunction. J Appl Physiol. Jan. 2004;96(1):25-31. Epub May 2, 2003.

(56) References Cited

OTHER PUBLICATIONS

Rustici et al., Molecular mapping and detoxification of the lipid A binding site by synthetic peptides. Science. Jan. 15, 1993;259(5093):361-5.

Salat et al., The relevance of plasminogen activator inhibitor 1 (PAI-1) as a marker for the diagnosis of hepatic veno-occlusive disease in patients after bone marrow transplantation. Leuk Lymphoma. Mar. 1999;33(1-2):25-32.

Saura et al., Microglial apolipoprotein E and astroglial apolipoprotein J expression in vitro: opposite effects of lipopolysaccharide. J Neurochem. Jun. 2003;85(6):1455-67.

Scarborough et al., Aggregation of platelets by muscle actin. A multivalent interaction model of platelet aggregation by ADP. Biochem Biophys Res Commun. Jun. 16, 1981;100(3):1314-9.

Schroder et al., Lipoteichoic acid (LTA) of *Streptococcus pneumoniae* and *Staphylococcus aureus* activates immune cells via Toll-like receptor (TLR)-2, lipopolysaccharide-binding protein (LBP), and CD14, whereas TLR-4 and MD-2 are not involved. J Biol Chem. May 2, 2003;278(18):15587-94. Epub Feb. 19, 2003.

Schultz et al., Animal and human models for sepsis. Ann Med. 2002;34(7-8):573-81.

Semba et al., Low serum selenium is associated with anemia among older adults in the United States. Eur J Clin Nutr. Jan. 2009;63(1):93-9. Published online Sep. 5, 2007. doi: 10.1038/sj.ejcn.1602889.

Sheu et al., Mechanisms involved in the antiplatelet activity of *Escherichia coli* lipopolysaccharide in human platelets. Br J Haematol. Oct. 1998;103(1):29-38.

Shimazu et al., MD-2, a molecule that confers lipopolysaccharide responsiveness on Toll-like receptor 4. J Exp Med. Jun. 7, 1999;189(11):1777-82.

Smith et al., Decreased plasma gelsolin levels in patients with Plasmodium falciparum malaria: a consequence of hemolysis? Blood. Jul. 1988;72(1):214-8.

Smith et al., Evidence for two pathways of protein kinase C induction of 2ar expression: correlation with mitogenesis. J Cell Physiol. Apr. 1989;139(1):189-95.

Smith et al., Quantitative measurement of plasma gelsolin and its incorporation into fibrin clots. J Lab Clin Med. Aug. 1987;110(2):189-95.

Spudich et al., The regulation of rabbit skeletal muscle contraction. I. Biochemical studies of the interaction of the tropomyosin-troponin complex with actin and the proteolytic fragments of myosin. J Biol Chem. Aug. 10, 1971;246(15):4866-71.

Stossel, From signal to pseudopod. How cells control cytoplasmic actin assembly. J Biol Chem. Nov. 5, 1989;264(31):18261-4.

Suhler et al., Decreased plasma gelsolin concentrations in acute liver failure, myocardial infarction, septic shock, and myonecrosis. Crit Care Med. Apr. 1997;25(4):594-8.

Sun et al., Gelsolin, a multifunctional actin regulatory protein. J Biol Chem. Nov. 19, 1999;274(47):33179-82.

Tauber et al., Antibiotic therapy, endotoxin concentration in cerebrospinal fluid, and brain edema in experimental *Escherichia coli* meningitis in rabbits. J Infect Dis. Sep. 1987;156(3):456-62.

Thomas et al., Biopanning of endotoxin-specific phage displayed peptides. Biochem Biophys Res Commun. Jul. 18, 2003;307(1):133-8.

Tobias et al., Control of lipopolysaccharide-high-density lipoprotein interactions by an acute-phase reactant in human serum. Infect Immun. Oct. 1985;50(1):73-6.

Tobias et al., Isolation of a lipopolysaccharide-binding acute phase reactant from rabbit serum. J Exp Med. Sep. 1, 1986;164(3):777-93.

Trautner et al., Role of biofilm in catheter-associated urinary tract infection. Am J Infect Control. May 2004;32(3):177-83. doi: 10.1016/j.ajic.2003.08.005.

Tuominen et al., Fluorescent phosphoinositide derivatives reveal specific binding of gelsolin and other actin regulatory proteins to mixed lipid bilayers. Eur J Biochem. Jul. 1999;263(1):85-92.

Van Oosten et al., Scavenger receptor-like receptors for the binding of lipopolysaccharide and lipoteichoic acid to liver endothelial and Kupffer cells. J Endotoxin Res. 2001;7(5):381-4.

Villa et al., Pattern of cytokines and pharmacomodulation in sepsis induced by cecal ligation and puncture compared with that induced by endotoxin. Clin Diagn Lab Immunol. Sep. 1995;2(5):549-53.

Visapää et al., Correlation of Ki-67 and gelsolin expression to clinical outcome in renal clear cell carcinoma. Urology. Apr. 2003;61(4):845-50.

Vreugdenhil et al., Lipopolysaccharide (LPS)-binding protein mediates LPS detoxification by chylomicrons. J Immunol. Feb. 1, 2003;170(3):1399-405.

Walker et al., Enhanced Pseudomonas aeruginosa biofilm development mediated by human neutrophils. Infect Immun. Jun. 2005;73(6):3693-701.

Wang et al., HMG-1 as a late mediator of endotoxin lethality in mice. Science. Jul. 9, 1999;285(5425):248-51.

Wanner et al., Atorvastatin in patients with type 2 diabetes mellitus undergoing hemodialysis. N Engl J Med. Jul. 21, 2005;353(3):238-48.

Ware et al., The acute respiratory distress syndrome. N Engl J Med. May 4, 2000;342(18):1334-49.

Watson et al., Genetic control of responses to bacterial lipopolysaccharides in mice. II. A gene that influences a membrane component involved in the activation of bone marrow-derived lymphocytes by lipipolysaccharides. J Immunol. May 1975;114(5):1462-8.

Weiner et al., The antimicrobial activity of the cathelicidin LL37 is inhibited by F-actin bundles and restored by gelsolin. Am J Respir Cell Mol Biol. Jun. 2003;28(6):738-45. Epub Dec. 30, 2003.

Wen et al., The plasma and cytoplasmic forms of human gelsolin differ in disulfide structure. Biochemistry. Jul. 30, 1996;35(30):9700-9.

Witke et al., Hemostatic, inflammatory, and fibroblast responses are blunted in mice lacking gelsolin. Cell. Apr. 7, 1995;81(1):41-51.

Workeneh et al., Review of muscle wasting associated with chronic kidney disease. Am J Clin Nutr. Apr. 2010;91(4):1128S-1132S. Epub Feb. 24, 2010.

Yamamoto et al., Human plasma gelsolin binds adenosine triphosphate. J Biochem. Oct. 1990;108(4):505-6.

Yamamura et al., Sphingosine-1-phosphate inhibits actin nucleation and pseudopodium formation to control cell motility of mouse melanoma cells. FEBS Lett. Mar. 11, 1996;382(1-2):193-7.

Yancey et al., Risk factors for neonatal sepsis. Obstet Gynecol. Feb. 1996;87(2):188-94.

Yatomi, Sphingosine 1-phosphate in vascular biology: possible therapeutic strategies to control vascular diseases. Curr Pharm Des. 2006;12(5):575-87.

Yin et al., Structure and biosynthesis of cytoplasmic and secreted variants of gelsolin. J Biol Chem. Apr. 25, 1984;259(8):5271-6.

Zuo et al., [Bacteriological study of chronic sinusitis]. Zhonghua Er Bi Yan Hou Tou Jing Wai Ke Za Zhi. Jul. 2005;40(7):524-7. English Abstract.

Extended European Search Report for Application No. EP 13186249.2 mailed Feb. 17, 2014.

Badid et al., Role of myofibroblasts during normal tissue repair and excessive scarring: interest of their assessment in nephropathies. Histol Histopathol. Jan. 2000;15(1):269-80.

Chebotareva et al., [The role of smooth muscle alpha-actin in development of renal fibrosis in patients with chronic glomerulonephritis]. Ter Arkh. 2006;78(5):17-21. Abstract Only.

Maury et al., Homozygosity for the Asn187 gelsolin mutation in Finnish-type familial amyloidosis is associated with severe renal disease. Genomics. Jul. 1992;13(3):902-3.

Extended European Search Report for EP 10185573.2 mailed May 16, 2012.

[No Author Listed] Choice of Control Group and Related Issues in Clinical Trials, E10. ICH Harmonised Tripartite Guideline. International Conference on Harmonisation of Technical Requirements for Registration of Pharmaceuticals for Human Use. Jul. 20, 2000. 35 pages.

[No Author Listed] E10 Choice of Control Group and Related Issues in Clinical Trials. Guidance for Industry. U.S. Department of Health and Human Services, Food and Drug Administration, Center for

(56) References Cited

OTHER PUBLICATIONS

Drug Evaluation and Research (CDER), and Center for Biologics Evaluation and Research (CBER). May 2001. 37 pages.

[No Author Listed] Pharmacokinetics in Patients with Impaired Hepatic Function: Study Design, Data Analysis, and Impact on Dosing and Labeling. Guidance for Industry. U.S. Department of Health and Human Services, Food and Drug Administration, Center for Drug Evaluation and Research (CDER), and Center for Biologics Evaluation and Research (CBER). May 2003. 19 pages.

Brettschneider et al., Tau protein level in cerebrospinal fluid is increased in patients with early multiple sclerosis. Mult Scler. Jun. 2005;11(3):261-5.

Bucki et al., Plasma gelsolin: function, prognostic value, and potential therapeutic use. Curr Protein Pept Sci. Dec. 2008;9(6):541-51.

Chavko et al., Lung injury and recovery after exposure to blast overpressure. J Trauma. Oct. 2006;61(4):933-42.

Chen, Multiple Sclerosis. Chinese Medicine Press. Jun. 30, 2000;67-73.

Dou, Immunocytology and Disease. Chapter 11. Chinese Medical Science and Technology Press. Sep. 30, 2004;404-415.

Grant et al., Reversal of Paralysis and Reduced Inflammation from Peripheral Administration of Amyloid-β in Th1- and Th17-Versions of Experimental Autoimmune Encephalomyelitis. Sci Transl Med. Aug. 1, 2012; 4(145): 145ra105.

Ji et al., Gelsolin levels are increased in the brain as a function of age during normal development in children that are further increased in Down syndrome. Alzheimer Dis Assoc Disord. Oct.-Dec. 2009;23(4):319-22.

KuŁakowska et al., Depletion of plasma gelsolin in patients with tick-borne encephalitis and Lyme neuroborreliosis. Neurodegener Dis. 2011;8(5):375-80.

Lee et al., Plasma gelsolin and circulating actin correlate with hemodialysis mortality. J Am Soc Nephrol. May 2009;20(5):1140-8. Epub Apr. 23, 2009.

Lee et al., Relationship of plasma gelsolin levels to outcomes in critically ill surgical patients. Ann Surg. Mar. 2006;243(3):399-403.

Lee et al., The potential role of plasma gelsolin in dialysis-related protein-energy wasting. Blood Purif. 2010;29(2):99-101. Epub Jan. 8, 2010.

Liao et al., Overexpression of gelsolin in human cervical carcinoma and its clinicopathological significance. Gynecol Oncol. Jan. 2011;120(1):135-44.

Matthay et al., Acute lung injury and the acute respiratory distress syndrome: four decades of inquiry into pathogenesis and rational management. Am J Respir Cell Mol Biol. Oct. 2005;33(4):319-27.

Mounzer et al., Relationship of admission plasma gelsolin levels to clinical outcomes in patients after major trauma. Am J Respir Crit Care Med. Nov. 1999;160(5 Pt 1):1673-81.

Pottiez et al., Mass spectrometric characterization of gelsolin isoforms. Rapid Commun Mass Spectrom. Sep. 15, 2010;24(17):2620-4.

Robinson, Amyloid beta reverses MS-like disease in mice. Is it time to reevaluate amyloid elsewhere? Sep. 2012:16-17.

Simon et al., A matched crossover design for clinical trials. Contemp Clin Trials. Sep. 2007;28(5):638-46.

Vasconcellos et al., Coordinated inhibition of actin-induced platelet aggregation by plasma gelsolin and vitamin D-binding protein. Blood. Dec. 15, 1993;82(12):3648-57.

Yang et al., Plasma Gelsolin Improves Lung Host Defense against Pneumonia by Enhancing Macrophage NOS3 Function. Am J Physiol Lung Cell Mol Physiol. May 8, 2015. doi:10.1152/ajplung.00094.2015.

Kozlova et al., [Use of fragmin in program hemodialysis of patients with terminal chronic renal failure]. Klin Med (Mosk). 2005;83(9):45-9. Russian. PubMed PMID: 16279040. Abstract only.

Vincent et al., Platelet function in sepsis. Crit Care Med. May 2002;30(5):S313-S317.

\* cited by examiner

DIAGNOSTIC AND THERAPEUTIC USES OF GELSOLIN IN RENAL FAILURE

RELATED APPLICATIONS

This application claims the benefit under 35 U.S.C. §119 (e) of U.S. provisional application Ser. No. 61/023,789, filed Jan. 25, 2008, the entire contents of which are incorporated by reference herein.

FEDERALLY SPONSORED RESEARCH

Some aspects of the present invention were made with support by grants from the United States National Institutes of Health (NIH) under NIH grants DK 71674 and DK 67397. The U.S. Government has certain rights in the invention.

FIELD OF INVENTION

The invention is directed to diagnostic and therapeutic uses of gelsolin.

BACKGROUND OF THE INVENTION

Chronic hemodialysis (HD) has drastically reduced the acute mortality of end-stage renal disease (ESRD). Nevertheless, chronic renal failure patients undergoing HD still die at a markedly accelerated rate. This adverse outcome appears early, with death ensuing far faster than in age-matched control populations within a year of initiating dialysis, and the most frequent causes of death are cardiovascular events and acute infections[1-3]. Patients with chronic renal failure exhibit manifestations of diffuse tissue injury, chronic inflammation, loss of muscle mass and hypoalbuminemia, and severe malnutrition, and all have been strongly linked with adverse outcomes[4-8]. The pathogenesis mediating the connection between the aggregate of these underlying conditions and accelerated mortality is largely unknown. Thus, the search for novel biomarkers that can reliably identify those ESRD and/or HD patients at increased risk of early death, and especially those biomarkers that are linked to potential therapies, may have significant clinical impact in improving the outcomes of this otherwise unfortunate population.

SUMMARY OF THE INVENTION

Plasma gelslolin (pGSN) is a sensitive marker of tissue injury with strong links to nutritional status, inflammation, and muscle mass, and importantly, with possible therapeutic utility[9-12]. pGSN is the extracellular variant of a protein, encoded on human chromosome[9], with cellular and secreted isoforms deployed by alternative mRNA splicing[13], Cellular gelsolin (cGSN) is a widely expressed mediator of cell shape change and motility through its regulated actin filament binding function[14]. Plasma gelsolin is an abundant plasma protein that circulates in healthy individuals at an average concentration of 250 mg/L[14], cGSN and pGSN are identical in primary structure and with respect to biochemical functions in vitro, except that pGSN contains an additional 25 amino acids at its amino terminal and has a processed signal sequence responsible for its secretion[13]. Many cell types secrete pGSN, although as the bulkiest body organ, striated muscle, accounts for most pGSN production. The amino acid sequence of pGSN is highly conserved between species, and no human anti-pGSN antibodies have been described[15].

Diverse conditions associated with acute tissue injury result in reductions in the circulating concentration of pGSN, the diminution in levels is proportional to the degree of injury, and critical extents of pGSN reduction are associated with adverse outcomes including death[11, 14, 16-18]. Although exposure of cytoplasmic actin to the extracellular environment due to membrane disruption in tissue and endothelial injury is likely the mechanism of pGSN depletion[19, 20], pGSN depletion also results from buffering a variety of circulating inflammatory mediators (e.g., platelet activating factor, lysophosphatidic acid, lipopolysaccharide)[12, 21] that potentially mediate adverse complications.

This invention is based, in part, on the discovery that, in chronic dialysis subjects, baseline plasma gelsolin levels are low and that gelsolin levels are inversely related to mortality risk such as from infectious causes or cardiac causes. Thus, the invention involves, in one aspect, using gelsolin to characterize a renal failure subject's mortality risk and to monitor the efficacy of therapy. The invention is also based on the discovery that, in chronic dialysis subjects, elevated plasma actin levels are related to mortality risk. Thus, the invention involves, in one aspect, using actin to characterize a renal failure subject's mortality risk and to monitor the efficacy of therapy. One correlate of these observations is that monitoring of plasma gelsolin levels and/or actin levels could become part of the management strategy of renal failure.

According to one aspect of the invention, a method for characterizing a renal failure subject's mortality risk is provided. The method comprises comparing a level of gelsolin from the subject to a predetermined value, and characterizing the subject's mortality risk based upon the level of gelsolin in comparison to the predetermined value. A level of gelsolin below the predetermined value indicates the subject has an increased mortality risk. In some embodiments, the predetermined value is about 190 nanograms/microliter (ng/µl) of plasma. In some embodiments, the predetermined value is about 150 ng/µl of plasma. In some other embodiments, the predetermined value is about 120 ng/µl of plasma. In some embodiments, a lower level of gelsolin indicates that the subject has a higher mortality risk. The method may further comprise obtaining the level of gelsolin from the subject.

According to another aspect of the invention, a method for characterizing a renal failure subject's mortality risk is provided. The method comprises comparing a level of actin from the subject to a predetermined value and characterizing the subject's mortality risk based upon the level of actin in comparison to the predetermined value. A level of actin above the predetermined value indicates the subject has an increased mortality risk. In some embodiments, the predetermined value is about 0.01 micrograms/milliliter (µg/ml) of plasma. In some embodiments, the predetermined value is about 0.1 µg/ml of plasma. In some embodiments, a higher level of actin correlates with a higher mortality risk. The method may further comprise obtaining the level of actin from the subject.

According to yet another aspect of the invention, a method for characterizing a renal failure subject's mortality risk is provided. The method comprises comparing a level of gelsolin from the subject to a first predetermined value to establish a first risk value and comparing a level of actin from the subject to a second predetermined value to establish a second risk value. The subject's mortality risk is characterized based upon the combination of the first risk value and the second risk value wherein the combination of the first risk value and second risk value establishes a third risk value different from said first and second risk values. In some embodiments, the first predetermined value is about 190 ng/µl of plasma. In some embodiments, the first predetermined value is about 150 ng/µl of plasma. In other embodiments, the first predetermined value is about 120 ng/µl of plasma. In some embodiments, the second predetermined value is about 0.01 µg/ml of plasma. In some embodiments, the predetermined value is about 0.1 µg/ml of plasma.

The method may further involve obtaining the level of gelsolin from the subject. In some embodiments, the method may further comprise obtaining the level of actin from the subject.

According to yet another aspect of the invention, a method for evaluating the efficacy of a therapy in a renal failure subject is provided. The method involves comparing a level of gelsolin from the subject to a predetermined value and determining whether the level of gelsolin is at or above the predetermined level said determination being indicative that the therapy is efficacious.

The steps of the method may be repeated so as to monitor the subject's levels of gelsolin over time. In some embodiments, the predetermined value is about 190 ng/µl of plasma. In some embodiments, the predetermined value is about 150 ng/µl of plasma. In other embodiments, the predetermined value is about 120 ng/µl of plasma.

According to yet another aspect of the invention, a method for treating a renal failure subject is provided. The method involves administering an effective amount of gelsolin to a subject in need of such a treatment to raise the level of gelsolin in the subject above a predetermined value. In some embodiments, the predetermined value is about 190 ng/µl of plasma. In some embodiments, the predetermined value is about 150 ng/µl of plasma. In other embodiments, the predetermined value is about 120 ng/µl of plasma.

The gelsolin may be plasma gelsolin pGSN), cytoplasmic gelsolin (cGSN), advillin, villin, capG, flightless proteins, fragmin, severin, adseverin, protovillin, and/or supervillin. The gelsolin may be administered orally, sublingually, buccally, intranasally, intravenously, intramuscularly, intrathecally, intraperitoneally, or subcutaneously.

According to still another aspect of the invention, a method for treating a renal failure subject having or at risk of developing an infection is provided. The method involves administering gelsolin to a subject in need of such a treatment in an effective amount to reduce the risk of the infection.

According to yet another aspect of the invention, a method of treatment to raise the level of gelsolin in a renal failure subject is provided. The method comprises instructing the renal failure subject in need of such a treatment to take an effective amount of gelsolin for the purpose of raising the level of gelsolin in the subject above a predetermined value. In some embodiments, the predetermined value is about 190 ng/µl of plasma. In some embodiments, the predetermined value is about 150 ng/µl of plasma. In other embodiments, the predetermined value is about 120 ng/µl of plasma.

The gelsolin may be plasma gelsolin (pGSN), cytoplasmic gelsolin (cGSN), advillin, villin, capG, flightless proteins, fragmin, severin, adseverin, protovillin, and/or supervillin. The gelsolin may be administered orally, sublingually, buccally, intranasally, intravenously, intramuscularly, intrathecally, intraperitoneally, or subcutaneously.

According to still another aspect of the invention, a method for treating a renal failure subject to raise the level of gelsolin in the subject is provided. The method comprises providing the subject with a package containing gelsolin, and providing the subject with indicia indicating that the gelsolin is for raising the level of gelsolin in the subject above a predetermined value. In some embodiments, the predetermined value is about 190 ng/µl of plasma. In some embodiments, the predetermined value is about 150 ng/µl of plasma. In other embodiments, the predetermined value is about 120 ng/µl of plasma.

The gelsolin may be plasma gelsolin (pGSN), cytoplasmic gelsolin (cGSN), advillin, villin, capG, flightless proteins, fragmin, severin, adseverin, protovillin, and/or supervillin. The gelsolin may be administered orally, sublingually, buccally, intranasally, intravenously, intramuscularly, intrathecally, intraperitoneally, or subcutaneously.

According to another aspect of the invention, a medical treatment product is provided. The product comprises a package containing gelsolin and indicia indicating that the gelsolin is for raising the level of gelsolin in a renal failure subject above a predetermined value. In some embodiments, the predetermined value is about 190 ng/µl of plasma. In some embodiments, the predetermined value is about 150 ng/µl of plasma. In other embodiments, the predetermined value is about 120 ng/µl of plasma.

The gelsolin may be plasma gelsolin (pGSN), cytoplasmic gelsolin (cGSN), advillin, villin, capG, flightless proteins, fragmin, severin, adseverin, protovillin, and/or supervillin. The gelsolin may be administered orally, sublingually, buccally, intranasally, intravenously, intramuscularly, intrathecally, intraperitonealy, or subcutaneously.

According to yet another aspect of the invention, the use of gelsolin in the manufacture of a medicament for raising the level of gelsolin in a renal failure subject above a predetermined value is provided. The gelsolin may be plasma gelsolin (pGSN), cytoplasmic gelsolin (cGSN), advillin, villin, capG, flightless proteins, fragmin, severin, adseverin, protovillin, and/or supervillin. The gelsolin may be administered orally, sublingually, buccally, intranasally, intravenously, intramuscularly, intrathecally, intraperitoneally, or subcutaneously.

The invention also provides for a method that comprises comparing a level of gelsolin in a renal failure subject to a predetermined value and, if the level of gelsolin is below the predetermined value, identifying the subject as having an increased mortality risk. In some embodiments, the method comprises advising the subject about the risk, treatment, or medical care. In some embodiments, the treatment comprises gelsolin. In some embodiments, the method comprises obtaining the level of gelsolin form the subject. In some embodiments, the predetermined value is about 190 ng/µl of plasma. In some embodiments, the predetermined value is about 150 ng/µl of plasma. In other embodiments, the predetermined value is about 120 ng/µl of plasma.

According to another aspect, the invention provides a method that comprises comparing a level of actin in a renal failure subject to a predetermined value and, if the level of actin is above the predetermined value, identifying the subject as having an increased mortality risk. In some embodiments, the method comprises advising the subject about the risk, treatment, or medical care. In some embodiments, the treatment comprises gelsolin. In some embodiments, the method comprises obtaining the level of actin form the subject. In some embodiments, the predetermined value is about 0.01 µg/ml of plasma. In some embodiments, the predetermined value is about 0.1 µg/ml of plasma.

According to yet another aspect, the invention provides a method that comprises performing an assay to detect a level of gelsolin in a renal failure subject, wherein the assay comprises a predetermined value that predicts increased mortality risk in the subject. In some embodiments, the method comprises advising the subject about the risk, treatment, or medical care. In some embodiments, the treatment comprises gelsolin. In some embodiments, the predetermined value is about 190 ng/μl of plasma. In some embodiments, the predetermined value is about 150 ng/μl of plasma. In other embodiments, the predetermined value is about 120 ng/μl of plasma.

According to still another aspect, the invention provides a method that comprises performing an assay to detect a level of actin in a renal failure subject, wherein the assay comprises a predetermined value that predicts increased mortality risk in the subject. In some embodiments, the method comprises advising the subject about the risk, treatment, or medical care. In some embodiments, the treatment comprises gelsolin. In some embodiments, the predetermined value is about 0.01 μg/ml of plasma. In some embodiments, the predetermined value is about 0.1 μg/ml of plasma.

The following embodiments apply to various aspects of the invention set forth herein unless indicated otherwise.

The level of gelsolin or actin may be in a body fluid of the subject. Examples of body fluids include but are not limited to blood, plasma, serum, urine, synovial fluid, cerebrospinal or alveolar fluid. In some important embodiments, the body fluid is plasma.

In some embodiments, the mortality is caused by an infection. The infection may be caused by a gram-positive bacterium, a gram-negative bacterium, an acid-fast bacillus, a spirochete, an actinomycete, a virus, a fungus, a parasite, *Ureoplasma* species, *Mycoplasma* species, *Chlamydia* species, or *Pneumocystis* species.

Examples of gram-positive bacteria include but are not limited to *Pasteurella* species, *Staphylococcus* species, *Streptococcus* species, *Bacillus anthracis*, *Corynebacterium* species, *Diphtheroids* species, *Listeria* species, *Erysipelothrix* species, and *Clostridium* species.

Examples of gram-negative bacteria include but are not limited to *Neisseria* species, *Branhamella* species, *Escherichia* species, *Enterobacter* species, *Proteus* species, *Pseudomonas* species, *Klebsiella* species, *Salmonella* species, *Shigella* species, *Serratia* species, *Acinetobacter* species, *Haemophilus* species, *Brucella* species, *Yersinia* species, *Francisella* species, *Pasturella* species, *Vibrio* cholera species, *Flavobacterium* species, *Pseudomonas* species, *Campylobacter* species, *Bacteroides* species, *Fusobacterium* species, *Calymmatobacterium* species, *Streptobacillus* species, and *Legionella* species.

The acid-fast bacillus may be a *Mycobacterium* species. The spirochete may be *Treponema* species, *Borrelia* species, or *Leptospira* species.

Examples of viruses include but are not limited to Retro viruses, human immunodeficiency viruses, Cytomegaloviruses, Picoma viruses, Polio viruses, hepatitis A virus, enteroviruses, Coxsackie viruses, rhinoviruses, echoviruses, Calciviruses, Toga viruses, equine encephalitis viruses, rubella viruses, Flaviviruses, dengue viruses, encephalitis viruses, yellow fever viruses, coronaviruses, Rhabdoviruses, vesicular stomatitis viruses, rabies viruses, Filoviruses, ebola virus, Paramyxo viruses, parainfluenza viruses, mumps virus, measles virus, respiratory syncytial virus, Orthomyxoviruses, influenza viruses, Hantaan viruses, bunga viruses, phleboviruses, Nairo viruses, Arena viruses, hemorrhagic fever viruses, reoviruses, orbiviruses, rotaviruses, Bimaviruses, Hepadnaviruses, Hepatitis B virus, parvoviruses, Papovaviruses, papilloma viruses, polyoma viruses, Adenoviruses, Herpes viruses, varicella zoster virus, Pox viruses, variola viruses, vaccinia viruses, Iridoviruses, African swine fever viruses, delta hepatitis virus, non-A, non-B hepatitis virus, Hepatitis C, Norwalk viruses, astroviruses, and unclassified viruses.

Examples of fungi include but are not limited to *Cryptococcus* species, *Histoplasma* species, *Coccidioides* species, *Paracoccidioides* species, *Blastomyces* species, *Chlamydia* species, *Candida* species, *Sporothrix* species, *Aspergillus* species, and fungus of mucormycosis.

Examples of parasites include but are not limited to *Plasmodium* species, *Toxoplasma* species, *Babesia* species, *Leishmania* species, and *Trypanosoma* species.

In some embodiments, the mortality is caused by a cardiovascular event. The cardiovascular event may be acute coronary syndrome, myocardial infarction, congestive heart failure, stroke, or sudden death.

In some embodiments, the subject is on dialysis. The dialysis may be hemodialysis or peritoneal dialysis. In some embodiments, the subject has end-stage renal disease (ESRD).

In some embodiments, the subject is otherwise free of indications calling for treatment. A subject free of indications calling for treatment with gelsolin is a subject who has no signs or symptoms calling for treatment with gelsolin. Gelsolin is indicated for the treatment of septic shock. Gelsolin is also indicated for the treatment of actin-related disorders such as Adult Respiratory Distress Syndrome (ARDS), fulminant hepatic necrosis, acute renal failure, muscle injury, disorders characterized by elevated levels of BUN and/or creatinine. Actin-related disorders are known to those of ordinary skill in the art.

In some embodiments, the first predetermined value may be a plurality of predetermined gelsolin level ranges, one of a plurality of ranges being below about 190 ng/μl of plasma and another of said ranges being above about 190 ng/μl of plasma, and the comparing step comprises determining in which of said plurality of predetermined gelsolin level ranges said subject's gelsolin level falls.

In some embodiments, the first predetermined value may be a plurality of predetermined gelsolin level ranges, one of a plurality of ranges being below about 150 ng/μl of plasma and another of said ranges being above about 150 ng/μl of plasma, and the comparing step comprises determining in which of said plurality of predetermined gelsolin level ranges said subject's gelsolin level falls. In some embodiments, the first predetermined value may be a plurality of predetermined gelsolin level ranges, one of a plurality of ranges being below about 120 ng/μl of plasma and another of said ranges being above about 120 ng/μl of plasma.

Each of the limitations of the invention can encompass various embodiments of the invention. It is, therefore, anticipated that each of the limitations of the invention involving any one element or combinations of elements can be included in each aspect of the invention. The invention is capable of other embodiments and of being practiced or of being carried out in various ways. Also, the phraseology and terminology used herein is for the purpose of description and should not be regarded as limiting. The use of "including", "comprising", or "having", "containing", "involving", and variations thereof herein, is meant to encompass the items listed thereafter and equivalents thereof as well as additional items.

These and other aspects of the inventions, as well as various advantages and utilities will be apparent with reference to the Detailed Description of the Invention. Each aspect of the invention can encompass various embodiments as will be understood.

All documents identified in this application are incorporated in their entirety herein by reference.

DETAILED DESCRIPTION

Figure 1:
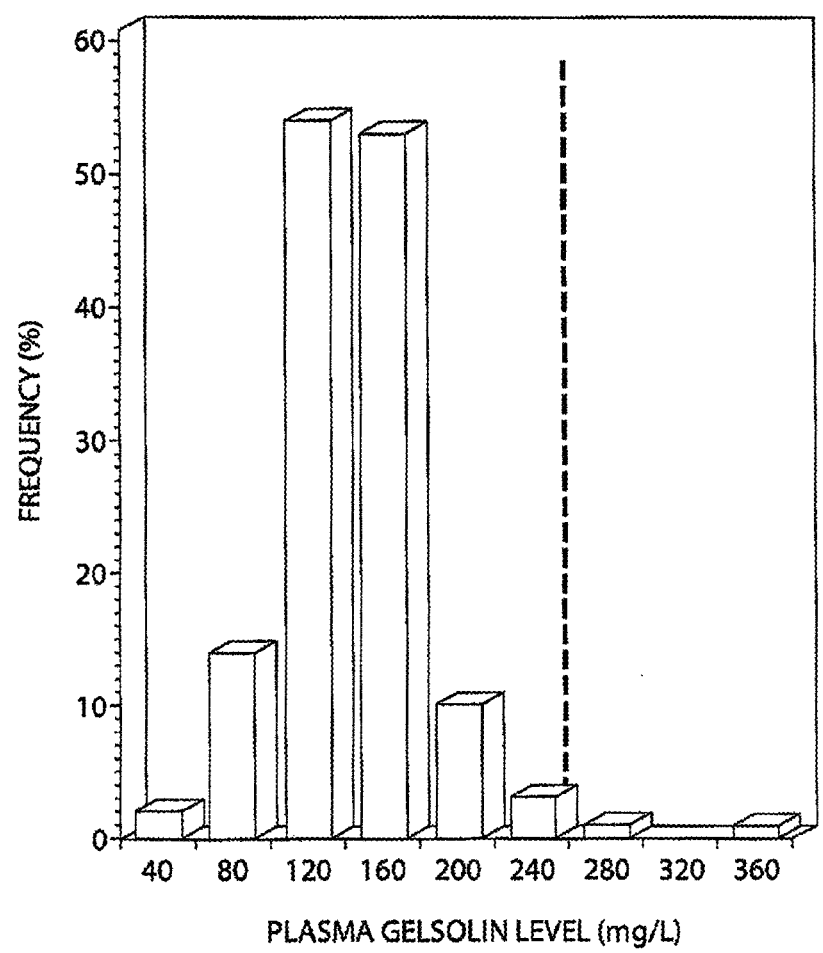
FIG. 1 is a histogram showing the distribution of plasma gelsolin in a random sampling of 150 ESRD subjects from throughout the United States. The dashed line represents the mean pGSN level of 250 mg/L in healthy controls.

This invention is based, in part, on the discovery that, in chronic dialysis subjects, baseline plasma gelsolin levels are low and gelsolin levels are inversely related to mortality (e.g., mortality from infectious or cardiac causes). The invention is also based, in part, on the discovery that, in chronic dialysis subjects, elevated plasma actin levels are directly related to mortality. Therefore, gelsolin depletion and/or excess actin predict mortality in renal failure subjects (e.g., chronic dialysis subjects). It is believed that gelsolin may be used to reduce mortality and/or to reduce the risk of infection in a renal failure subject (e.g., chronic dialysis subject).

Thus, the invention involves, in some aspects, administering gelsolin to a renal failure subject (e.g., chronic dialysis subject) to raise the level of gelsolin in the subject and to reduce mortality and/or to reduce the risk of infection in the renal failure subject (e.g., chronic dialysis subject). The term "treat" or "treatment" is intended to include prophylaxis, amelioration, prevention or cure from the condition.

As used herein, the term "gelsolin" encompasses wild type gelsolin (GenBank accession No.: X04412), isoforms, analogs, variants, fragments or functional derivatives of gelsolin.

Gelsolin (GSN), unlike other mammalian proteins, has both cytoplasmic (cGSN) and secreted or exported isoforms, also called plasma gelsolin pGSN), which are derived by alternative splicing of the message from a single gene (Sun et at *J. Biol. Chem.* 274:33179-33182 (1999)). As used herein, gelsolin isoforms include versions of gelsolin with some small differences in their amino acid sequences, usually a splice variant or the result of some posttranslational modification.

Gelsolin encompasses native as well as synthetic and recombinant gelsolin. Gelsolin is an abundant secretory protein (Yin, H. L., Kwiatkowski, D. J., Mole, J. E. & Cole, F. S. (1984) *J Biol Chem* 259, 5271-6). The exported isoform of gelsolin, pGSN, has 25 additional amino acids and originates from alternative splicing of a single gene (Kwiatkowski, D. J., Stossel, T. P., Orkin, S. H., Mole, J. E., Colten, H. R. & Yin, H. L. (1986) *Nature* 323, 455-8). Recombinant human gelsolin (rhGSN) (Biogen IDEC, Inc., Cambridge, Mass.) is produced in *E. coli*, and though it has the same primary structure as the native protein, under standard conditions of purification, it differs from natural human plasma gelsolin by a disulfide bond that is present in the natural protein. The recombinant protein is, therefore, properly oxidized after purification, and its structure and functions are indistinguishable from human plasma gelsolin (Wen et. al., *Biochemistry* 35:9700-9709 (1996)). In some of the therapeutic aspects and embodiments of the invention, the use of rhGSN is preferred. In some of the diagnostic aspects and embodiments of the invention, the use of pGSN is preferred.

A "gelsolin analog" refers to a compound substantially similar in function to either the native gelsolin or to a fragment thereof. Gelsolin analogs include biologically active amino acid sequences substantially similar to the gelsolin sequences and may have substituted, deleted, elongated, replaced, or otherwise modified sequences that possess bioactivity substantially similar to that of gelsolin. For example, an analog of gelsolin is one which does not have the same amino acid sequence as gelsolin but which is sufficiently homologous to gelsolin so as to retain the bioactivity of gelsolin. Bioactivity can be determined, for example, by assaying gelsolin's ability to stimulate actin nucleation. Gelsolin bioactivity assays are known to those of ordinary skill in the art.

A gelsolin "variant" is meant to refer to a compound that is substantially similar in structure and bioactivity either to native gelsolin, or to a fragment thereof. The term variant encompasses the gelsolin family of proteins. The gelsolin family of proteins is a group of actin binding proteins sharing repeats of about 15 kDa homologous domains that adopt a similar fold. Examples gelsolin family proteins include but are not limited to advillin, villin, capG, flightless proteins, fragmin, severin, adseverin, protovillin, and supervillin.

A gelsolin "fragment" is meant to include any portion of a gelsolin molecule which provides a segment of gelsolin which maintains the bioactivity of gelsolin; the term is meant to include gelsolin fragments which are made from any source, such as, for example, from naturally-occurring peptide sequences, synthetic or chemically-synthesized peptide sequences, and genetically engineered peptide sequences.

A "functional derivative" of gel solin is a derivative which possesses a bioactivity that is substantially similar to the bioactivity of gelsolin. By "substantially similar" is meant activity which is quantitatively different but qualitatively the same. For example, a functional derivative of gelsolin could contain the same amino acid backbone as gelsolin but also contains other modifications such as post-translational modifications such as, for example, bound phospholipids, or covalently linked carbohydrate, depending on the necessity of such modifications for the performance of the diagnostic assay or therapeutic treatment. As used herein, the term is also meant to include a chemical derivative of gelsolin. Such derivatives may improve gelsolin's solubility, absorption, biological half life, etc. The derivatives may also decrease the toxicity of gelsolin, or eliminate or attenuate any undesirable side effect of gelsolin, etc. Chemical moieties capable of mediating such effects are disclosed in Remington's Pharmaceutical Sciences (1980). Procedures for coupling such moieties to a molecule such as gelsolin are well known in the art. The term "functional derivative" is intended to include the "fragments," "variants," "analogues," or "chemical derivatives" of gelsolin.

The invention involves in some aspects, methods for treating a renal failure subject (e.g., chronic dialysis subject). The gelsolin is administered in an amount effective to raise the level of gelsolin and or to reduce the level of actin in the subject.

A response to a treatment method of the invention can be determined, for example, by measuring plasma or blood gelsolin and/or plasma or blood actin to determine whether plasma or blood gelsolin levels are increased and/or plasma or blood actin levels are decreased as a result of the treatment. Tests and methods for measuring plasma or blood gelsolin and/or actin and interpreting results of such tests are known to those of ordinary skill in the art.

In another aspect of the invention, a method for monitoring therapy in a subject is provided. The method involves obtaining a level of gelsolin and/or a level of actin in a subject undergoing therapy. The level of gelsolin is compared to a predetermined value corresponding to a control level of gelsolin (e.g., in an apparently healthy population). The level of actin is compared to a predetermined value corresponding to a control level of actin (e.g., in an apparently healthy population). A determination of whether the level of gelsolin and/or actin is at, below or above a predetermined level will indicate of whether the subject would benefit from continued therapy with the same therapy or would benefit from a change in therapy. For example, in some embodiments, a determination that the level of gelsolin is at or above a predetermined level and/or the level of actin is at or below a predetermined level will indicate that the subject would benefit from continued therapy with the same therapy. In some embodiments, a determination that the level of gelsolin is at or below a predetermined level and/or the level of actin is at or above a predetermined level indicates that the subject would benefit from change in therapy. In some embodiments, obtaining a level of gelsolin and/or actin is repeated so as to monitor the subject's levels of gelsolin and/or actin over time.

A change in therapy with gelsolin refers to an increase in the dose of the gelsolin, a switch from one gelsolin to another gelsolin, a switch from gelsolin to another agent, the addition of another agent to the gelsolin therapeutic regimen, or a combination thereof.

According to another aspect of the invention, a method for evaluating the efficacy of a therapy of renal failure in a subject is provided. The method comprises comparing a level of gelsolin to a predetermined value and determining whether the level of gelsolin is at or above a predetermined level said determination being indicative that the therapy is efficacious. In some embodiments, the method comprises comparing a level of actin to a predetermined value and determining whether the level of actin is at or below a predetermined level said determination being indicative that the therapy is efficacious.

In some embodiments, the subject may have been undergoing the therapy for at least 1, 2, 3, 4, 5, 6, 7 days or more. In some embodiments, the subject may have been undergoing the therapy for at least 1, 2, 3, 4, 5, 6, 7, 8, 9, 10, 11, 12 weeks or more. In some embodiments, the subject may have been undergoing the therapy for at least 3, 4, 5, 6, 7, 8, 9, 10, 11, 12 months or more.

One aspect of the invention is directed to the measurement of gelsolin levels and/or actin levels to guide treatments in order to improve outcome in subjects. Levels of gelsolin and/or actin have predictive value for response to treatments to reduce the risk of mortality in a renal failure subject. Subjects who would benefit from this aspect of this invention are renal failure subjects who are undergoing therapy to reduce the risk of mortality (e.g., from infections or cardiac causes) and to raise the level of gelsolin. A subject on-therapy is a subject who already has been diagnosed with renal failure (e.g., a subject on chronic hemodialysis) and is in the course of treatment with a therapy. The therapy can be any of the therapeutic agents used in the treatment of renal failure. Therapeutic agents used in the treatment of renal failure are known to those of ordinary skill in the art. The therapy also can be non-drug treatments. In important embodiments, the therapy is one which increases levels of gelsolin and/or decreases levels of actin. In some embodiments, the therapy is a therapy with gelsolin. The subject most likely to benefit from this invention is a human subject on-therapy (e.g., a human subject with renal failure on therapy for renal failure) and who has a gelsolin level at or below about 190 ng/μl (ng/μl) of plasma or who has an actin level at or above about 0.01 μg/ml of plasma. In some embodiments, the human subject on-therapy has a gelsolin level at or below about 150 ng/μl of plasma. In some embodiments, the human subject on-therapy has a gelsolin level at or below about 120 ng/μl of plasma. In some embodiments, the human subject on-therapy has an actin level at or above about 0.1 μg/ml of plasma.

In some embodiments, the subject already has or had an infection. A subject who has or has had a primary (first) bacterial, viral, fungal, parasitic, or protozoal infection may be at an elevated risk of a secondary (second) infection. In some embodiments, the subject has not had a primary infection, but is at an elevated risk of having an infection because the subject has one or more risk factors to have an infection. Examples of risk factors for a primary infection include: immunosuppression, immunocompromise, age, trauma, burns (e.g., thermal burns), surgery, foreign bodies, and cancer. The degree of risk of an infection depends on the multitude and the severity or the magnitude of the risk factors that the subject has. Risk charts and prediction algorithms are available for assessing the risk of an infection in a subject based on the presence and severity of risk factors.

In some embodiments, the treatment is gelsolin. Gelsolin may be administered alone, in a pharmaceutical composition or combined with other therapeutic regimens. Gelsolin and optionally other therapeutic agent(s) may be administered simultaneously or sequentially. When the other therapeutic agents are administered simultaneously they can be administered in the same or separate formulations, but are administered at the same time. The other therapeutic agents may be administered sequentially with one another and with gelsolin when the administration of the other therapeutic agents and the gelsolin is temporally separated. The separation in time between the administration of these compounds may be a matter of minutes or it may be longer.

In practicing certain methods of the present invention, a level of gelsolin in a subject is obtained. This level then is compared to a predetermined value, wherein the level of gelsolin in comparison to the predetermined value is indicative of the likelihood that the subject will benefit from continued therapy. The subject then can be characterized in terms of the net benefit likely to be obtained from a change in therapy.

The level of the gelsolin for the subject can be obtained by any art recognized method. Typically, the level is determined by measuring the level of gelsolin in a body fluid, for example, blood, serum, plasma, lymph, saliva, urine, and the like. The level can be determined by ELISA, or other immunoassays or other conventional techniques for determining the presence of gelsolin. Conventional methods may include sending a sample(s) of a subject's body fluid to a commercial laboratory for measurement. Methods for measuring gelsolin are described herein.

The invention also involves comparing the level of gelsolin and/or the level of actin for the subject with a predetermined value. The predetermined value can take a variety of forms. It can be a single cut-off value, such as a median or mean. It can be established based upon comparative groups, such as, for example, where the risk in one defined group is double the risk in another defined group. It can be a range, for example, where the tested population is divided equally (or unequally) into groups, such as a low-risk group, a medium-risk group and a high-risk group, or into quartiles, the lowest quartile being subjects with the highest risk and the highest quartile being subjects with the lowest risk, or into tertiles the lowest tertile being subjects with the highest risk and the highest tertile being subjects with the lowest risk. The predetermined value may be a cut-off value which is predetermined by the fact that a group having a gelsolin level less than the cut-off value demonstrates a statistically significant increase in the mortality risk as compared to a comparative group. In some embodiments the comparative group is a group having a higher level of gelsolin.

The predetermined value can depend upon the particular population of subjects selected. Accordingly, the predetermined values selected may take into account the category in which a subject falls. Appropriate ranges and categories can be selected with no more than routine experimentation by those of ordinary skill in the art. The preferred body fluids are plasma and blood. In some embodiments, the predetermined value of gelsolin is about 190 ng/µl of plasma. In some embodiments, the predetermined value of gelsolin is about 150 ng/µl of plasma. In some embodiments, the predetermined value of gelsolin is about 120 ng/µl of plasma. The predetermined value will depend, of course, upon the characteristics of the subject population in which the subject lies. In characterizing risk, numerous predetermined values can be established.

Commercial sources which produce reagents for assays for gelsolin. These include, for example, Cytoskeleton (Denver, Colo.), Sigma (St. Louis, Mo.) and Calbiochem (San Diego, Calif.)

In practicing certain methods of the present invention, it is required to obtain a level of actin in a subject. This level then is compared to a predetermined value, wherein the level of actin in comparison to the predetermined value is indicative of the likelihood that the subject will benefit from continued therapy. The subject then can be characterized in terms of the net benefit likely to be obtained from a change in therapy.

The level of the actin for the subject can be obtained by any art recognized method. Typically, the level is determined by measuring the level of actin in a body fluid, for example, blood, serum, plasma, lymph, saliva, urine, and the like. The level can be determined as described in the Example below, or other assays or other conventional techniques for determining the presence of actin. Conventional methods may include sending a sample(s) of a subject's body fluid to a commercial laboratory for measurement.

The invention also involves comparing the level of actin for the subject with a predetermined value. The predetermined value can take a variety of forms. It can be a single cut-off value, such as a median or mean. It can be established based upon comparative groups, such as, for example, where the risk in one defined group is double the risk in another defined group. It can be a range, for example, where the tested population is divided equally (or unequally) into groups, such as a low-risk group, a medium-risk group and a high-risk group, or into quartiles, the lowest quartile being subjects with the lowest risk and the highest quartile being subjects with the highest risk, or into tertiles the lowest tertile being subjects with the lowest risk and the highest tertile being subjects with the highest risk. The predetermined value may be a cut-off value which is predetermined by the fact that a group having an actin level higher than the cut-off value demonstrates a statistically significant increase in mortality risk as compared to a comparative group.

The predetermined value can depend upon the particular population of subjects selected. Accordingly, the predetermined values selected may take into account the category in which a subject falls. Appropriate ranges and categories can be selected with no more than routine experimentation by those of ordinary skill in the art. In some embodiments, the predetermined value of actin is about 0.01 µg/ml of plasma. In some embodiments, the predetermined value of actin is about 0.1 µg/ml of plasma. The predetermined value will depend, of course, upon the characteristics of the subject population in which the subject lies. In characterizing risk, numerous predetermined values can be established.

The invention provides methods for determining whether a subject will benefit from continued therapy or would benefit from a change in therapy. The benefit is typically a reduction in the signs and symptoms or complications of renal failure (e.g., infectious or cardiovascular complications). Signs, symptoms, manifestations and complications of renal failure are known to those of ordinary skill in the art.

These methods have important implications for patient treatment and also for the clinical development of new therapies. Determining whether a subject will benefit from continued therapy or would benefit from a change in therapy is clinically useful. One example of clinical usefulness of the methods of this invention includes identifying subjects who are less likely or more likely to respond to a therapy. The methods of the invention are also useful in predicting or determining that a subject would benefit from continued therapy or would benefit from a change in therapy. Health care practitioners select therapeutic regimens for treatment based upon the expected net benefit to the subject. The net benefit is derived from the risk to benefit ratio. The present invention permits the determination of whether a subject will benefit from continued therapy or would benefit from a change in therapy, thereby aiding the physician in selecting a therapy.

Another example of clinical usefulness, in the case of human subjects for example, includes aiding clinical investigators in the selection for clinical trials of subjects with a high likelihood of obtaining a net benefit. It is expected that clinical investigators now will use the present invention for determining entry criteria for clinical trials.

A subject who would benefit from continued therapy is a subject whose on-therapy level of gelsolin reaches a certain predetermined value or whose level of gelsolin is increasing. Predetermined values of gelsolin are described above. A subject who would benefit from a change in therapy is a subject whose on-therapy level of the gelsolin did not reach a certain predetermined value or whose on-therapy level of gelsolin is not increasing.

A subject who would also benefit from continued therapy is a subject whose on-therapy level of actin reaches a certain predetermined value or whose level of actin is decreasing. Predetermined values of actin are described above. A subject who would benefit from a change in therapy is a subject whose on-therapy level of the actin did not reach a certain predetermined value or whose on-therapy level of actin is not decreasing.

As used herein, a "change in therapy" refers to an increase or decrease in the dose of the existing therapy, a switch from one therapy to another therapy, an addition of another therapy to the existing therapy, or a combination thereof. A switch from one therapy to another may involve a switch to a therapy with a high risk profile but where the likelihood of expected benefit is increased. In some embodiments, preferred therapies are therapies that increase the level(s) of gelsolin and/or that decrease the level(s) of actin. A subject who would benefit from a change in therapy by increasing the dose of the existing therapy is a subject who, for example, was on the therapy but was not receiving the maximum tolerated dose or the maximum allowed dose of the therapy and whose level of gelsolin and/or actin did not reach a certain predetermined value. In such instances the dose of the existing therapy is increased until the level of gelsolin and/or actin reaches a certain predetermined value. In some instances, the dose of the existing therapy is increased from the existing dose to a higher dose that is not the maximum tolerated dose nor the maximum allowed dose of the therapy. In other instances, the dose is increased to the maximum tolerated or to the maximum allowed dose of the therapy. A subject who would benefit from a change in therapy by decreasing the dose of the existing therapy is, for example, a subject whose on-therapy level of gelsolin and/or actin reaches or can reach a certain predetermined value with a lower dose of the therapy.

A subject who would benefit from a switch from one therapy to another therapy is, for example, a subject who was on the maximum tolerated dose or the maximum allowed dose of the therapy and whose level of gelsolin and/or actin did not reach a certain predetermined value. Another example is a subject was not on the maximum tolerated or the maximum allowed dose of the therapy but was determined by a health care practitioner to more likely benefit from another therapy. Such determinations are based, for example, on the development in the subject of unwanted side effects on the initial therapy or a lack of response to the initial therapy.

A subject who would benefit from a change in therapy by the addition of another therapy to the existing therapy is, for example, a subject who was on a therapy but whose level of gelsolin and/or actin did not reach a certain predetermined value. In such instances, another therapy is added to the existing therapy. The therapy that is added to the existing therapy can have a different mechanism of action in increasing the level of gelsolin and/or decreasing the level of actin than the existing therapy. In some instances, a combination of the aforementioned changes in therapy may be used.

The invention also provides methods for determining the efficacy of a therapy. The efficacy is typically the efficacy of the therapy in increasing the level of gelsolin and/or decreasing the level of actin. This is sometimes also referred to as a positive response or a favorable response. Efficacy can be determined by a gelsolin blood test(s) and/or actin blood test(s) to determine whether gelsolin level(s) increased or actin level(s) decreased as a result of therapy. The invention also provides methods for deciding on the course of a therapy in a subject undergoing therapy. Such a course of therapy is decided on the basis of the level(s) of gelsolin and/or the level(s) of actin.

The gelsolin or actin measurement is typically reported in ng/μl (nanograms/microliter), μM/L (micromoles/Liter), mg/dl (milligrams/deciliter), mg/L (milligrams/Liter) or μg/ml (microgram/milliliter).

The amount of a treatment may be varied for example by increasing or decreasing the amount of gelsolin or pharmacological agent or a therapeutic composition, by changing the therapeutic composition administered, by changing the route of administration, by changing the dosage timing and so on. The effective amount will vary with the condition being treated, the age and physical condition of the subject being treated, the severity of the condition, the duration of the treatment, the nature of the concurrent therapy (if any), the specific route of administration, and like factors are within the knowledge and expertise of the health practitioner. For example, an effective amount can depend upon the duration the subject has had the renal failure.

An effective amount is a dosage of the therapeutic agent sufficient to provide a medically desirable result. An effective amount may also, for example, depend upon the degree to which a subject has abnormally decreased levels of gelsolin and/or abnormally elevated levels of actin. It should be understood that the therapeutic agents of the invention are used, for example, to treat or prevent complications (e.g., infectious or cardiac) in a renal failure subject. Thus, for example, an effective amount is that amount which can lower the risk of, slow or perhaps prevent altogether the development of an infection or a cardiac complication in a renal failure subject.

The factors involved in determining an effective amount are well known to those of ordinary skill in the art and can be addressed with no more than routine experimentation. In some embodiments, a maximum dose of the pharmacological agents of the invention (alone or in combination with other therapeutic agents) be used, that is, the highest safe dose according to sound medical judgment. It will be understood by those of ordinary skill in the art however, that a subject may insist upon a lower dose or tolerable dose for medical reasons, psychological reasons or for virtually any other reason(s).

The therapeutically effective amount of a pharmacological agent of the invention is that amount effective to increase the level of gelsolin and/or decrease the level of actin or to treat or prevent an infection or a cardiac complication in a renal failure subject. For example, the desired response may be inhibiting the progression of an infection or a cardiac complication. This may involve only slowing the progression of the infection or the cardiac complication temporarily, although more preferably, it involves halting the progression of the infection or the cardiac complication. This can be monitored by routine diagnostic methods known to those of ordinary skill in the art. The desired response to treatment may be an increase in the level of plasma gelsolin or a decrease in the plasma level of actin.

The pharmacological agents used in the methods of the invention are preferably sterile and contain an effective amount of gelsolin for producing the desired response in a unit of weight or volume suitable for administration to a subject. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg, preferably from about 0.1 mg/kg to about 500 mg/kg, and most preferably from about 0.2 mg/kg to about 250 mg/kg, in one or more dose administrations daily, for one or more days.

Gelsolin and optionally other therapeutics may be administered per se or in the form of a pharmaceutically acceptable salt.

Various modes of administration are known to those of ordinary skill in the art which effectively deliver the pharmacological agents of the invention to a desired tissue, cell, or bodily fluid. The administration methods are discussed elsewhere in the application. The invention is not limited by the particular modes of administration disclosed herein. Standard references in the art (e.g., *Remington's Pharmaceutical Sciences,* 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride, chlorobutanol, parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle (e.g., saline, buffer, or sterile pyrogen-free water) before use.

Compositions suitable for oral administration may be presented as discrete units, such as capsules, tablets, pills, lozenges, each containing a predetermined amount of the active compound (e.g., gelsolin). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, sorbitol or cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of gelsolin or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi-particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, gelsolin may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (C) and carboxymethyl cellulose (CMC). Polyvinyl pyrrolidone (PVP) and hydroxypropylmethyl cellulose (HPMC) could both be used in alcoholic solutions to granulate the therapeutic.

An anti-frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non-ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of gelsolin either alone or as a mixture in different ratios.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of gelsolin. Gelsolin is delivered to the lungs of a mammal while inhaling and traverses across the lung epithelial lining to the blood stream. Other reports of inhaled molecules include Adjei et al., 1990, Pharmaceutical Research, 7:565-569; Adjei et al., 1990, International Journal of Pharmaceutics, 63:135-144 (leuprolide acetate); Braquet et al., 1989, Journal of Cardiovascular Pharmacology, 13(suppl. 5):143-146 (endothelin-1); Hubbard et al., 1989, Annals of Internal Medicine, Vol. III, pp. 206-212 (a1-antitrypsin); Smith et al., 1989, J. Clin. Invest. 84:1145-1146 (a-1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482-3488 (interferon-γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass.

All such devices require the use of formulations suitable for the dispensing of gelsolin. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified gelsolin may also be prepared in different formulations depending on the type of chemical modification or the type of device employed.

Formulations suitable for use with a nebulizer, either jet or ultrasonic, will typically comprise gelsolin dissolved in water at a concentration of about 0.1 to 25 mg of biologically active gelsolin per mL of solution. The formulation may also include a buffer and a simple sugar (e.g., for gelsolin stabilization and regulation of osmotic pressure). The nebulizer formulation may also contain a surfactant, to reduce or prevent surface induced aggregation of the gelsolin caused by atomization of the solution in forming the aerosol.

Formulations for use with a metered-dose inhaler device will generally comprise a finely divided powder containing the gelsolin suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing gelsolin and may also include a bulking agent, such as lactose, sorbitol, sucrose, or mannitol in amounts which facilitate dispersal of the powder from the device, e.g., 50 to 90% by weight of the formulation. The gelsolin should most advantageously be prepared in particulate form with an average particle size of less than 10 mm (or microns), most preferably 0.5 to 5 mm, for most effective delivery to the distal lung.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The therapeutic agent(s), including specifically but not limited to gelsolin, may be provided in particles. Particles as used herein means nano or micro particles (or in some instances larger) which can consist in whole or in part of gelsolin or the other therapeutic agent(s) as described herein. The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the gelsolin in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug there from. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

For topical administration to the eye, nasal membranes, mucous membranes or to the skin, the gelsolin may be formulated as ointments, creams or lotions, or as a transdermal patch or intraocular insert or iontophoresis. For example, ointments and creams can be formulated with an aqueous or oily base alone or together with suitable thickening and/or gelling agents. Lotions can be formulated with an aqueous or oily base and, typically, further include one or more emulsifying agents, stabilizing agents, dispersing agents, suspending agents, thickening agents, or coloring agents. (See, e.g., U.S. Pat. No. 5,563,153, entitled "Sterile Topical Anesthetic Gel", issued to Mueller, D., et al., for a description of a pharmaceutically acceptable gel-based topical carrier.)

In general, the gelsolin or the actin-binding molecule is present in a topical formulation in an amount ranging from about 0.01% to about 30.0% by weight, based upon the total weight of the composition. Preferably, the gelsolin is present in an amount ranging from about 0.5 to about 30% by weight and, most preferably, the gelsolin is present in an amount ranging from about 0.5 to about 10% by weight. In one embodiment, the compositions of the invention comprise a gel mixture to maximize contact with the surface of the localized pain and minimize the volume and dosage necessary to alleviate the localized pain. GELFOAM® (a methylcellulose-based gel manufactured by Upjohn Corporation) is a preferred pharmaceutically acceptable topical carrier. Other pharmaceutically acceptable carriers include iontophoresis for transdermal drug delivery.

The invention also contemplates the use of kits. In some aspects of the invention, the kit can include a pharmaceutical preparation vial, a pharmaceutical preparation diluent vial, and gelsolin. The vial containing the diluent for the pharmaceutical preparation is optional. The diluent vial contains a diluent such as physiological saline for diluting what could be a concentrated solution or lyophilized powder of gelsolin. The instructions can include instructions for mixing a particular amount of the diluent with a particular amount of the concentrated pharmaceutical preparation, whereby a final formulation for injection or infusion is prepared. The instructions may include instructions for treating a subject with an effective amount of gelsolin. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The present invention is further illustrated by the following Example, which in no way should be construed as further limiting. The entire contents of all of the references (including literature references, issued patents, published patent applications, and co-pending patent applications) cited throughout this application are hereby expressly incorporated by reference.

EXAMPLE

Overview:

Accelerated Mortality on Renal Replacement (ArMORR) is a nationally representative prospective cohort study of patients that initiated chronic hemodialysis at U.S. dialysis centers operated by Fresenius Medical Care, North America (FMC, Lexington, Mass.). Information collected prospectively included patient demographics, comorbidities at the initiation of hemodialysis, laboratory tests (performed by Spectra East, Rockland, N.J.), intravenous therapies, and clinical outcomes. Data were entered into a central database by physicians and nurses at the point of care, with rigorous quality assurance/quality control auditing mandated by FMC[22, 23]. This study was approved by the Institutional Review Board of the Massachusetts General Hospital.

Study Population:

Between Jul. 1, 2004 and Jun. 30, 2005, 10,044 incident hemodialysis patients representing 1056 U.S. dialysis units were prospectively enrolled into ArMORR. All incident hemodialysis patients who initiated therapy at a US-based Fresenius unit were eligible for inclusion in the ArMORR cohort. A random sample of 150 patients with an available baseline (collected within 14 days of initiating chronic hemodialysis) blood sample for plasma gelsolin and actin, and serum high sensitivity C reactive protein were included in the study Of these 150 subjects, 41 (27%) died within 365 days of initiating dialysis and 109 survived for at least 365 days. To efficiently study the effects of pGSN levels on survival, we also performed a nested case-control study defining cases as ESRD subjects who died within 365 days of initiating dialysis and controls as those who survived for at least 365 days. To increase power, we added the next 75 consecutive ArMORR participants who died within 365 days of initiating dialysis (n=116 total cases) to the original sample to create a case-control sample of 1:1 ratio with a total of 225 subjects. We aimed to include a similar number of CVD deaths and infectious deaths (defined below). Subsequently, 2 patients were found not to have sufficient blood sample, hence they were excluded, leaving a total of 223 subjects to study. With a case-control sample of 223 and a 1:1 ratio, we had >80% power to detect an odds ratio of at least 2 among patients with pGSN deficiency (e.g., lowest category if examined in tertiles) compared to those with higher levels.

Ascertainment of Exposures and Outcomes:

The primary exposure was baseline pGSN levels, and the primary outcome was overall one-year mortality. pGSN was examined as a continuous and binomial (based on the median levels in the random) variable, and we examined pGSN in tertile analyses. In addition to overall mortality, we also defined outcomes with cardiovascular (e.g., died of diseases of the circulatory system, ICD-9 390-459.9; hypertensive diseases, 401-405; ischemic heart disease, 410-414; acute myocardial infarction, 410; and cerebrovascular disease, 430-438) and infectious causes of mortality (e.g., bacterial, fungal, and viral pneumonias, ICD-9 480.0-487.8; empyema, 510.0; lung abscess, 513.0; sepsis, severe sepsis, and septic shock, 038, 995-996, 785) within one year of initiating chronic HD. Death was confirmed by discharge diagnosis reports from the individual dialysis centers.

The primary covariate of interest was plasma actin levels that were semi-quantitated (see below). Other covariates included age, race, sex, body mass index, assigned cause of renal failure (e.g., diabetes, hypertension, glomerulonephritis, polycystic kidney disease or other), blood pressure, body mass index, vascular access at initiation (arteriovenous fistula, graft or veno-venous catheter), and dialysis dose (Kt/V) as we have done in prior analyses[22, 23]. Baseline blood levels of albumin, creatinine, calcium, phosphorus, and platelet and white blood cell count were analyzed. Serum level of high sensitivity CRP (hsCRP) at baseline using standard techniques (N Latex CRP assay, Dade Behring) was also measured.

Plasma Gelsolin (pGSN):

pGSN was measured by its ability to stimulate actin nucleation as described previously[24]. This functional assay is highly reproducible and detects total levels of pGSN irrespective of whether it is complexed to actin or other pGSN ligands. In brief, baseline plasma was diluted 1:5 fold in 0.1 M KCl, 0.2 mM $MgCl_2$, 1 mM EGTA, 0.5 mM ATP, 0.5 mM β-mercaptoethanol, and 10 mM Tris-HCl buffer, pH 7.4 (Buffer B). Of the diluted plasma sample, 5 μl was added to 280 μl Buffer B supplemented with 1.5 mM $CaCl_2$ and 0.4 μM Phallacidin in 6×50 mm borosilicate culture tubes. The actin polymerization reaction was initiated by adding 15 μl 20 μM pyrene actin[25] in 0.5 mM ATP, 5 mM β-mercaptoethanol, 0.2 mM $CaCl_2$, 0.2 mM Tris-HCl buffer, pH 7.4 (Buffer A). Polymerization was monitored for 200 seconds in a spectrofluorimeter at excitation and emission wavelengths of 366 and 386 nm respectively. pGSN concentrations were estimated from a standard curve using purified recombinant human pGSN synthesized in *E. coli*. All measurements were performed with the laboratory technician blinded to the outcomes.

Detecting Circulating Actin:

Plasma was diluted 1:10 fold in phosphate buffered saline (PBS) and then analyzed by E-PAGE 48 8% gel system as per manufacturer's instructions (Invitrogen, Carlsbad, Calif.). Each sample was heated at 70° C. for 10 minutes in β-mercaptoethanol-containing sample buffer prior to loading onto an E-PA GE 48 gel, then transferred to nitrocellulose membranes. After blocking the membrane in 5% non-fat dry milk in Tris-buffered saline (TBS) with 0.05% Tween 20, primary anti-β actin antibodies (AC-15, Sigma, St. Louis, Mo.) were added at 1:2000 dilution and incubated at room temperature for 1 hr. Bound primary antibodies were probed with HRP-linked anti-rabbit IgG's (Santa Cruz Biotechnology, Santa Cruz, Calif.) at 1:2000 dilution. Chemiluminescence of HRP was developed with Super Signal West Pico Kit (Pierce, Rockford, Ill.). The presence of actin was defined as the appearance on the blots of discrete bands co-migrating with purified rabbit skeletal muscle actin (Cytoskeleton, Denver, Colo.). The specificity of the actin on the Western blots was confirmed by subjecting 10 randomly selected samples to mass spectrometry (Beth Israel Deaconess Medical Center Mass Spectrometry Core Facility). All measurements were performed with the laboratory technician blinded to the outcomes.

Statistical Analyses:

We used two-sample t tests and Fisher's exact to compare demographic and laboratory characteristics and pGSN and levels and the presence of actin at the initiation of dialysis among the patients who died and those that did not. To examine whether routine laboratory tests were associated with pGSN levels, we used Spearman correlation coefficients. We used linear regression models to examine independent relationships between pGSN and other covariates. Univariate analysis of survival was performed on the initial random sampling of 150 subjects using Kaplan-Meier curves with log-rank tests after dividing baseline values of pGSN into binary or tertile values. The total number of subjects censored for recovery of renal function, kidney transplantation, or lost to follow up because they transferred their care to a non-FMC center was less than 8%.

Multivariate logistic regression models were used to examine the independent association between baseline pGSN and all-cause, cardiovascular, and infectious causes of one-year mortality. We included covariates in the multivariate models that have been associated with mortality on dialysis in previous studies[22, 23] and those that were significantly different among cases and controls in the current study. We also adjusted all models for C-reactive protein levels given their relationship with vascular disease and mortality among hemodialysis patients[5]. Data points on individual covariates were missing in <5% of subjects; for the multivariate analyses, these covariates were treated as categorical variables with an additional category for missing values. Otherwise, continuous variables were analyzed on a continuous scale. We examined the relationship between pGSN and outcomes stratified by plasma levels of actin given the biological relationship of these two measures. Finally, first order interactions were examined between pGSN and covariates (pGSNx covariate) in univariate and multivariate models, and when significant (p≤0.1) interaction was detected, stratified models were presented. Finally, Analyses were performed using SAS 9.1 (Cary, N.C.) and two-sided p-values <0.05 were considered statistically significant.

Results:

Baseline Characteristics: The initial sample of 150 ESRD subjects represented 148 separate dialysis centers across the U.S. The baseline characteristics of these subjects are presented in Table 1 and resemble baseline characteristics of larger populations of ESRD subjects at the initiation of chronic hemodialysis[26]. The distribution of baseline pGSN levels is shown in FIG. 1. Mean pGSN levels were 140±42 mg/L, and only 2 (1%) of subjects demonstrated baseline levels at or above 250 mg/L, the mean level reported in healthy volunteers (dashed line in FIG. 1 and Table 5)[14, 27]. Plasma gelsolin levels correlated inversely with age (r=−0.18, p<0.01) and baseline measures of muscle mass and nutrition, such as serum creatinine (r=0.26, p<0.01) and albumin levels (r=0.34, p<0.01). The correlation between pGSN and body mass index was 0.02 (p>0.05). When baseline hs-CRP levels were examined in tertiles, those with the lowest levels of hs-CRP demonstrated the highest levels of pGSN: tertile 1, hs-CRP<12 mg/L, pGSN 145±39 mg/l; tertiles 2 & 3, hs-CRP≥12 mg/L, pGSN 131±53 mg/L, P=0.048). Linear regression analyses confirmed that among the continuous variables in Table 1 that met a p value threshold of 0.1, only serum albumin was independently correlated with pGSN levels (p<0.01).

Figure 2:
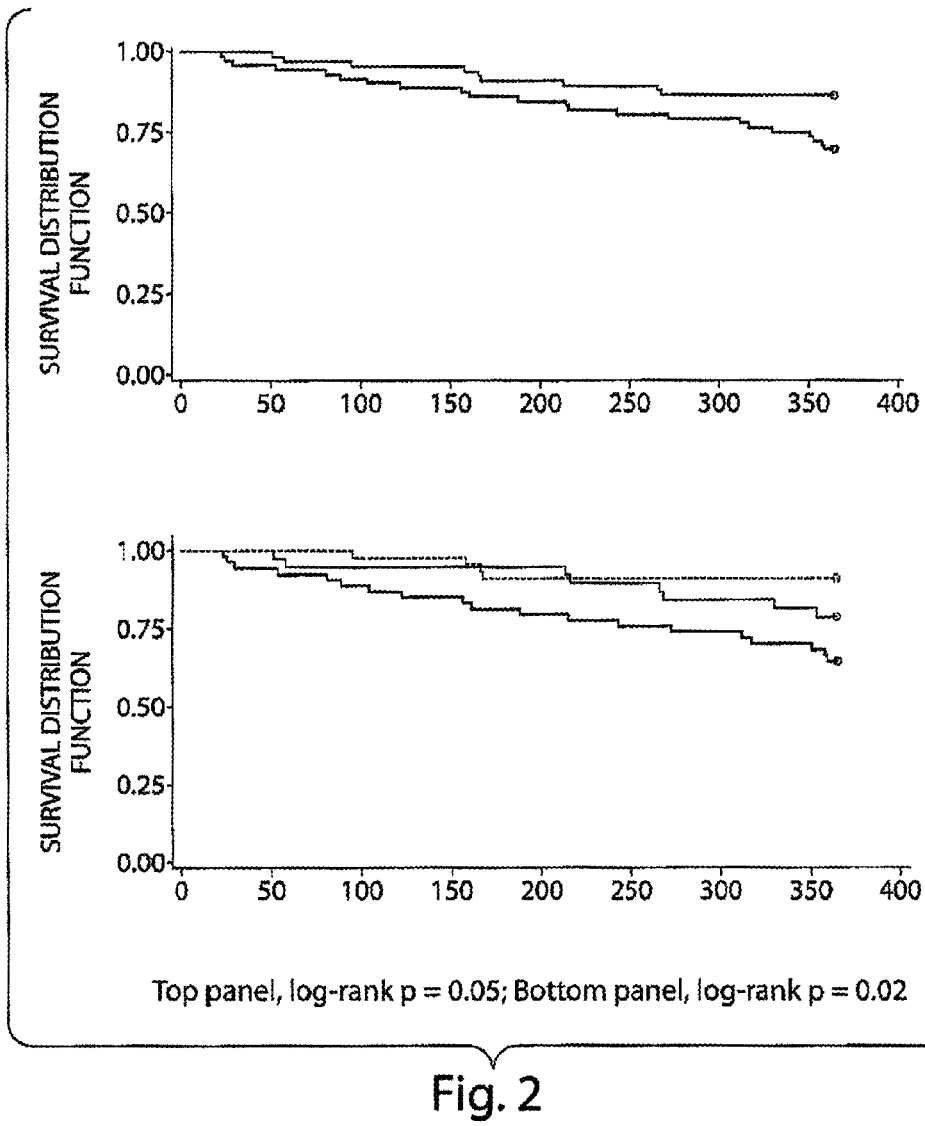
FIG. 2 are two graphs showing the 1-year survival among chronic dialysis patients according to indicated median plasma gelsolin level (top panel) or according to baseline levels of plasma gelsolin subdivided into indicated tertiles (bottom panel). Kaplan Meier analysis of one-year survival according to baseline pGSN levels categorized by the median level (top panel; log-rank $p=0.05$) and tertiles (Bottom panel; log-rank $p=0.02$.) in the controls.

Plasma pGSN and One Year Survival: The median pGSN level among the 150 subjects was 141 mg/L (IQR 116-161 mg/l). Kaplan-Meier analyses of 1-year survival according to binary pGSN levels (< or ≥141 mg/L) demonstrated a significant survival difference according to baseline pGSN levels (FIG. 2—top panel). Similarly, dividing pGSN into tertiles revealed a graded relationship with baseline pGSN levels and one-year mortality (FIG. 2—bottom panel). The median day of death among those that died within one-year was 188 days (IQR 89-297 days).

The case-control sample of 223 patients was subsequently utilized to examine one-year survival. Baseline characteristics according to one-year outcomes are presented in Table 2. Those who died within one year were slightly older, were more likely to have an intravenous catheter as their initial vascular access (compared with arterio-venous fistula or graft), and had lower serum albumin and higher white blood cell counts at baseline. These baseline differences have been reported in previous studies of hemodialysis mortality[26]. Mean pGSN levels were significantly lower in patients who died (117±38 mg/L) compared to survivors (147±42 mg/L, p<0.001). Baseline pGSN levels did not differ between cardiovascular (n=59, 116±41 mg/L) and infectious (n=55, 117±34 mg/L, p=0.91) deaths.

Multivariable Analysis of Mortality:

We next examined the relationship of pGSN levels and 1-year mortality after adjusting for important covariates and potential confounders (Table 3). For every 10 mg/L reduction in baseline pGSN, the risk for subsequent mortality was increased by 15% (95% CI, 7-23%). The risk among those with the lowest baseline levels (tertile 1, <130 mg/L) demonstrated the highest risk for one-year all cause and infectious causes of mortality. Both findings were significant and demonstrated a strong linear trend. The results for cardiovascular causes of death were less significant. In these analyses, hs-CRP did not significantly associate with one-year mortality. In addition, serum creatinine, which was significant on univariate analysis, was no longer significant once the model was adjusted for pGSN.

Serum albumin, a measure of nutrition and muscle mass, has been strongly associated with ESRD mortality[28]. We then examined the effect of serum albumin on the multivariable models and noted that while the point estimates for each tertile of pGSN were modestly larger without serum albumin, the level and direction of significance did not change by adding serum albumin. Alternatively, including or excluding pGSN gave the following results with serum albumin: excluding pGSN, tertile 1 (serum albumin <3.2 mg/dl), OR 3.0, 95% CI 1.1-6.4; tertile 2 (3.2-3.6 mg/dl), OR 1.1, 0.5-2.4; tertile 3 (>3.6 mg/dl), OR 1.0 (ref); including pGSN, tertile 1, OR 2.0, 95% CI 0.8-4.9; tertile 2, OR 1.0, 0.5-2.4; tertile 3, OR 1.0 (ref). When serum albumin was modeled as a continuous variable, it remained significant even after adjustment for pGSN (excluding pGSN, OR 0.32 for each 1 mg/dl increase of serum albumin, 95% CI 0.15-0.67; including pGSN, OR 0.39, 95% CI 0.18-0.83). Therefore, addition of pGSN to the models attenuated but did not extinguish association between serum albumin and mortality.

Figure 3:
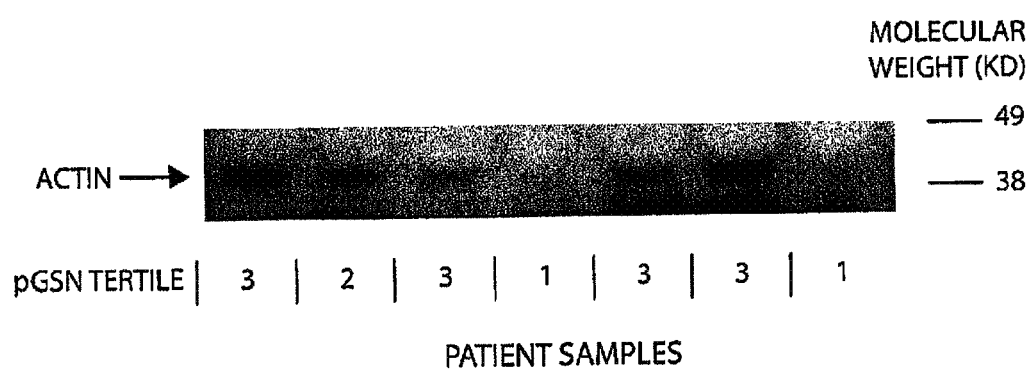
FIG. 3 is a picture of a Western blot detecting plasma actin from subjects with indicated pGSN tertiles.

Circulating Actin, pGSN, and Mortality:

Western blotting was used to detect plasma actin. Although actin polypeptides were clearly visible as discrete bands on the blots, and these bands were verified as authentic actin by mass spectrometry, the presence of non-specific background staining due to high plasma protein concentrations and the relatively low affinity of anti-actin antibodies precluded detailed quantification of actin protein in the samples. Sixty-nine percent of patients had circulating actin at baseline, and diabetic renal failure patients were more likely to have circulating actin (85%) than patients with other causes of renal failure (59%, P<0.001). Compared to those with no actin, pGSN levels were lower in patients with actin (141±36 mg/L vs. 127±45 mg/L, respectively, P=0.02) (FIG. 3) which was consistent with previous results in sepsis samples[10].

We therefore examined the relationship of baseline plasma actin presence vs. absence) and 1-year mortality. In univariate analysis, the presence of actin conferred a 3.5 fold (95% CI 1.9-6.4) increase in risk for death at one year. This relationship persisted on multivariate analyses (OR 4.6, 95% CI 2.0-10.5). The presence of diabetic renal failure, which significantly associated with early mortality on univariate analyses (OR 1.8, 95% CI 1.1-3.0), became non-significant after adjusting for circulating actin (OR 1.3, 95% CI 0.7-2.3). Given that pGSN binds actin released by tissue damage and may abrogate actin-induced injury,[14, 20, 27, 42] we hypothesized that low pGSN and elevated actin would increase risk of adverse outcomes.

Figure 4:
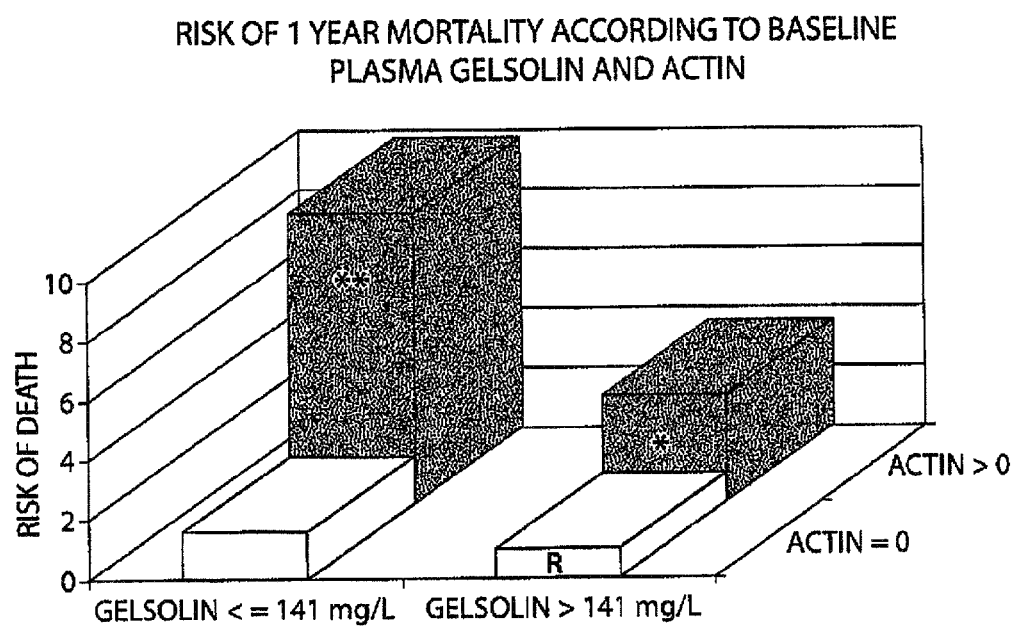
FIG. 4 is a histogram showing the risk of 1-year mortality according to baseline plasma gelsolin and actin levels. Compared to those with elevated baseline pGSN (+pGSN) and no detectable actin (−actin), the multivariable risk of one-year death among those with low baseline pGSN (−pGSN) and detectable actin (+actin) was significantly elevated: −pGSN, +actin, OR 9.8, 95% CI 2.9-33.5; +pGSN, +actin, OR 3.6, 95% CI 1.0-13.5; −pGSN, −actin, OR 1.6, 95% CI 0.3-7.7; +pGSN, −actin, OR 1.0 (ref). * $p=0.05$, ** $p=0.01$.

We next examined the risk for one-year mortality according to pGSN levels and presence or absence of actin (FIG. 4). In these analyses, pGSN was divided into a binomial variable as above. These results suggested that the combined parameters of low pGSN and detectable actin were potentially associated synergistically rather than additively to risk of death.

Figure 5:
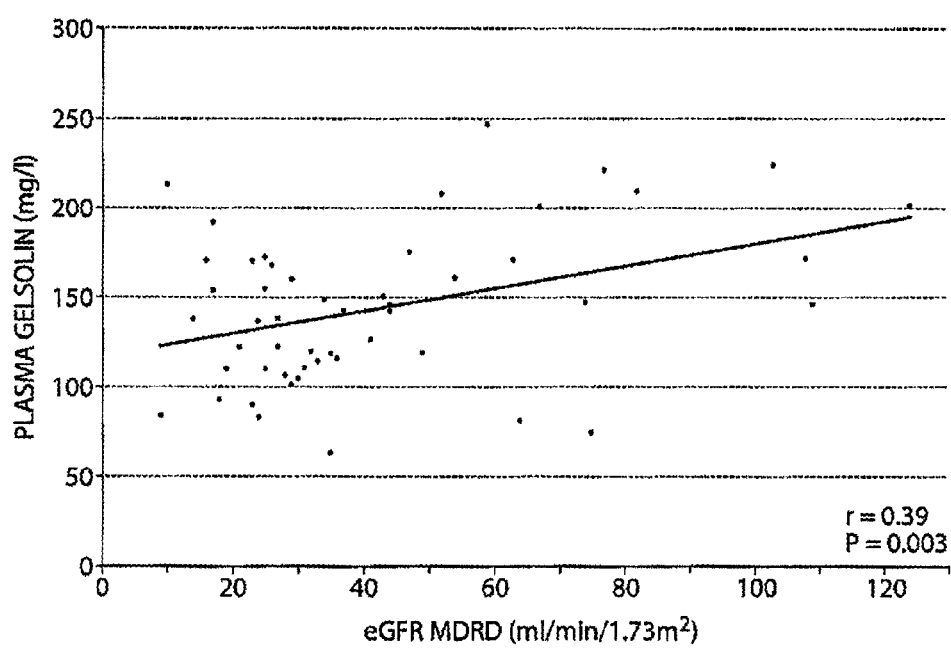
FIG. 5 is a graph showing the correlation between baseline plasma gelsolin (pGSN) levels and estimated glomerular filtration rate in 53 patients with chronic kidney disease.
Figure 6:
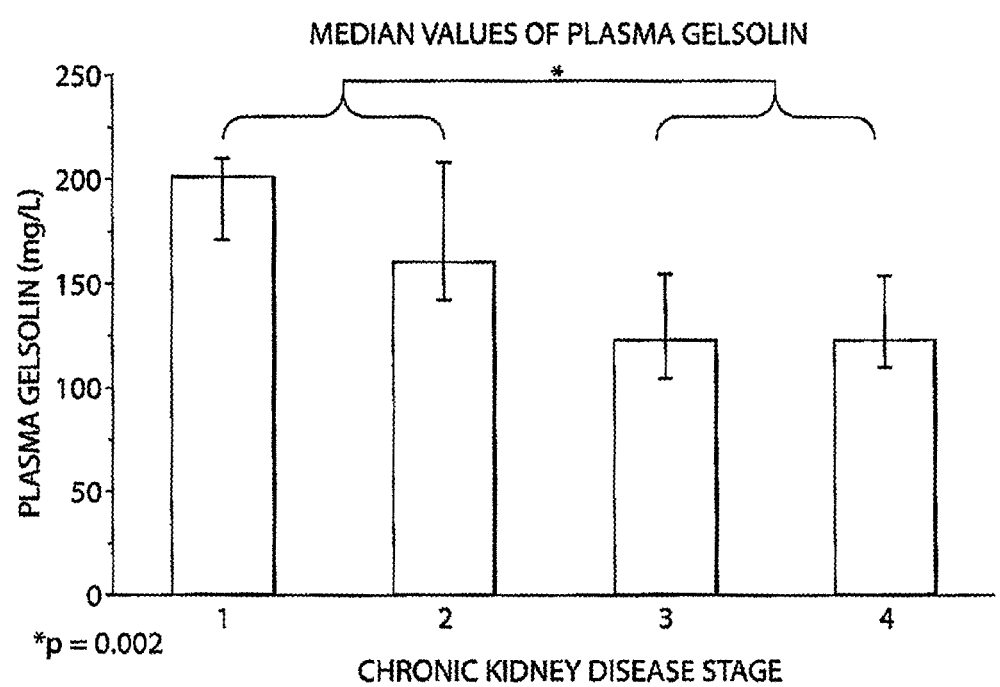
FIG. 6 is a histogram showing median pGSN levels in patients with chronic kidney disease. Stage 1 (n=5), estimated glomerular filtration rate (eGFR)>90 ml/min/1.73 m$^2$; Stage 2 (n=11), eGFR 60-89 ml/min/1.73 m$^2$; Stage 3 (n=18), eGFR 30-59 ml/min/0.73 m$^2$; Stage 4 (n=19), eGFR 15-29 ml/min/1.73 m$^2$. Error bars represent inter-quartile ranges.

Veno-Venous Catheter and Mortality:

We sought additional effect modifications by including interaction terms (e.g., pGSN x covariate) in multivariable models with covariates of interest. The only additional interaction suggested was vascular access type (P=0.04). Although veno-venous catheter vascular access associates with an increased risk for early mortality[29], deciphering those most susceptible to death has been challenging. Patients initiating hemodialysis with a catheter (129±49 mg/L) or with an arterio-venous fistula or graft (136±32 mg/L, P=0.24) did not differ at baseline by pGSN levels, nor by the frequency of circulating actin (71% vs. 68%, respectively, P=0.67). Nevertheless, a veno-venous catheter appeared to influence one-year mortality risk (Table 4). Amongst patients with a veno-venous catheter, those with low pGSN and detectable circulating actin had a marked increase in overall mortality compared to those with high pGSN and no detectable actin (OR 25.9, 95% CI 4.3-157.0).

pGSN, Circulating Actin, and Chronic Kidney Disease:

pGSN levels correlated directly with estimated glomerular filtration rate (r=0.39, P=0.003) in subjects with chronic kidney disease not on dialysis (FIG. 5). Males (153±43 mg/L) tended to have higher levels of pGSN compared with females (136±52 mg/L, p=0.09). Levels in late stages of kidney disease (e.g., stages 3 and 4) were comparable to those found at the initiation of chronic hemodialysis. However, these levels were significantly lower than in samples obtained from stages 1 and 2 (P=0.002) (FIG. 6). The frequency of circulating actin was 11% in this pre-dialysis cohort, in contrast to 69% in the dialysis cohort (P<0.001).

Discussion:

Patients initiating hemodialysis have pGSN levels reduced to an average 30-50% lower than found in healthy controls. pGSN declines with progressive renal disease, suggesting mechanisms upstream of chronic dialysis initiation account for pGSN reduction. Following the initiation of chronic hemodialysis, pGSN demonstrated a graded, inverse relationship with adverse outcomes—the lower the level, the higher the risk for one-year mortality.

Figure 7:
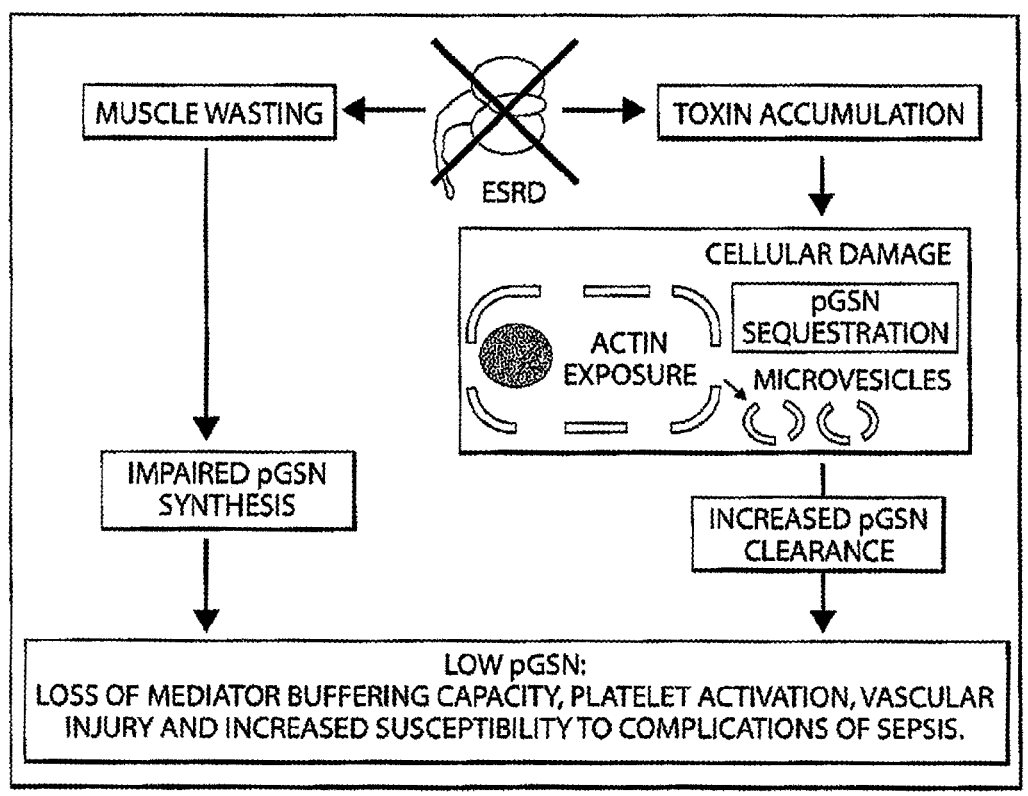
FIG. 7 is a picture of some possible mechanisms for pGSN depletion and its consequences in chronic renal failure. Chronic renal failure inhibits pGSN synthesis and accelerates clearance. Muscle is the major source of pGSN biosynthesis, and the reduction of muscle mass associated with chronic renal failure would reduce net pGSN production. The failure to eliminate toxins in renal failure causes widespread tissue, especially endothelial, destruction leading to exposure of cytoplasmic actin into the plasma and pGSN sequestration in broken cells. In addition, release of inside-out membrane vesicles with attached actin filaments from damaged cells would result in detectable circulating actin, and circulating actin accelerates pGSN clearance. Low pGSN results in impaired buffering of inflammatory mediators such as platelet-activating factor, promoting vascular complications, and rendering patients susceptible to the lethal effects of sepsis.

It is believed that pGSN sequestration at sites of injury or clearance with circulating actin may be the principal causes of decreased pGSN concentrations following acute insults. These factors may also contribute to diminished pGSN in ESRD, but, in addition, impairment of synthesis may be important. For example, uremia is characterized by increased activity of the ubiquitin-proteasome pathway[43], and recently increased activity of this pathway has been linked to increased degradation of cGSN, the intracellular isoform of pGSN.[44] Moreover, since the molecular weight of pGSN is 93 kDA, pGSN is unlikely to be cleared by hemodialysis. As highlighted in FIG. 7, combination of decreased production and increased consumption due to ongoing tissue injury in dialysis patients are some possible etiologies of the decreased circulating levels of pGSN in end-stage renal failure subjects. pGSN synthesis is constitutive and does not increase like acute phase reactants in inflammation.[35] Since muscle is a major source of pGSN, correlations with serum albumin and creatinine suggest protein-energy wasting characteristic of ESRD may contribute to pGSN reduction.[4, 8, 28, 36, 37, 38, 43, 45, 46] pGSN attenuates the otherwise strong relationship between serum creatinine and albumin and hemodialysis mortality,[8] suggesting at least a partial overlap between these parameters in explaining mortality.

Patients at greatest risk for death with the lowest pGSN levels were those with detectable circulating actin. Actin has been detectable in plasma of patients with acute lung or liver injury,[14] patients with severe trauma, and even in healthy blood donors.[47] Circulating actin in over two-thirds of hemodialysis patients is consistent with wide spread tissue injury and excess muscle protein catabolism reported in patients with ESRD.[43, 48, 49, 50] Most (85%) patients with diabetic renal failure, a group with widespread endothelial cell injury and markedly elevated mortality rates,[1, 51, 52] had circulating actin, and it was interesting to find that adjustment for circulating actin eliminated the relationship between diabetes status and mortality that has been previously reported.[41] Circulating actin has been documented in patients with acute respiratory distress syndrome[20] and in animal models of sepsis (Table 5).[11] In contrast to pGSN depletion, detectable circulating actin was far less prevalent in advanced renal disease prior to dialysis, suggesting that dialysis itself, possibly resulting from acute hemodynamic fluxes or dialysis membrane bioincompatibilies[53], may contribute to tissue damage releasing actin into the circulation.

pGSN depletion may link muscle wasting, tissue injury, inflammation and death due to cardiovascular events and sepsis in ESRD. pGSN depletion may indeed characterize other chronic wasting states. pGSN avidly binds inflammatory mediators including platelet-activating factor, lysophosphatidic acid, lipoteichoic acid, aβ peptide and lipopolysaccharide endotoxin and decreases the effects of these agonists on target cells.[12, 30, 31, 32, 33] Loss of buffering of these mediators due to pGSN depletion could exacerbate vascular disease and its contribution to mortality. Toxic effects of circulating actin on the vasculature might also be important.[20, 54] Deficiency of pGSN may also worsen the outcome of superimposed infection.[10, 11, 34] Low pGSN and circulating actin conferred a markedly increased risk for early mortality in catheter compared to graft- or fistula-managed patients. Attenuation of pGSN's ability to disrupt actin-containing biofilms may be one mechanism low pGSN and elevated actin predispose to adverse outcomes in catheter-instrumented patients.[55, 56] Moreover, actin impairs the activity of leukocyte-derived cationic anti-microbial polypeptides known as defensins.[42]

TABLE 1

Baseline Characteristics

|  | N = 150 |
|---|---|
| Age (Years) | 64 ± 15 |
| Female (%) | 45 |
| Race (%) | |
| White | 53 |
| Black | 41 |
| Other | 6 |
| BMI (kg/m2) | 28 ± 19 |
| Diabetes Mellitus (%) | 20 |
| Etiology of Renal Failure (% Diabetes) | 43 |
| Vascular Access (% Catheter) | 57 |
| Systolic blood pressure (mmHg) | 145 ± 20 |
| Diastolic blood pressure (mmHg) | 74 ± 13 |
| Albumin (g/dl) | 3.5 ± 0.4 |
| Calcium (mg/dl) | 8.5 ± 0.8 |
| Phosphorus (mg/dl) | 4.6 ± 1.4 |
| Creatinine (mg/dl) | 6.4 ± 2.6 |
| eKT/V | 1.3 ± 0.4 |
| Hemoglobin (g/dl) | 10.0 ± 1.4 |
| hs- C reactive protein (mg/L) | 29 ± 38 |
| White blood cell count (cells/mcl) | 7.5 ± 2.6 |
| Platelets (cells/dl) | 236 ± 95 |

TABLE 2

Baseline Characteristics of the Case-Control Sample*

| N | Cases N = 114 | Controls N = 109 | p-value |
|---|---|---|---|
| Age (Years) | 67 ± 13 | 63 ± 15 | 0.02 |
| Female (%) | 45 | 45 | 0.99 |
| Race (%) | | | 0.22 |
| White | 59 | 47 | |
| Black | 36 | 47 | |
| Other | 5 | 6 | |
| BMI (kg/m2) | 26 ± 3 | 27 ± 7 | 0.20 |
| Diabetes Mellitus (%) | 21 | 20 | 0.86 |
| Etiology of Renal Failure (% Diabetes) | 50 | 36 | 0.03 |
| Vascular Access (% Catheter) | 70 | 46 | <0.01 |
| Systolic blood pressure (mmHg) | 140 ± 25 | 145 ± 20 | 0.02 |
| Diastolic blood pressure (mmHg) | 71 ± 14 | 74 ± 12 | 0.05 |
| Albumin (g/dl) | 3.2 ± 0.6 | 3.5 ± 0.5 | <0.01 |
| Calcium (mg/dl) | 8.3 ± 0.7 | 8.4 ± 0.8 | 0.20 |
| Phosphorus (mg/dl) | 4.4 ± 1.4 | 4.6 ± 1.3 | 0.05 |
| Creatinine (mg/dl) | 5.5 ± 2.6 | 6.5 ± 2.6 | 0.01 |
| eKt/V | 1.3 ± 0.3 | 1.3 ± 0.4 | 0.56 |
| Hemoglobin (g/dl) | 10.1 ± 1.3 | 10.0 ± 1.4 | 0.40 |
| **hs - C reactive protein (mg/L) | 20 (7-47) | 13 (3-24) | 0.20 |
| White blood cell count (cells/mcl) | 8.7 ± 4.1 | 7.5 ± 2.6 | 0.01 |
| Platelets (cells/dl) | 210 ± 84 | 236 ± 95 | 0.08 |

*Values are frequencies or means ± standard deviations.
**hs - C reactive protein (hs-CRP) reported as median values and interquartile range (IQR, 25%-75%).

TABLE 3

Multivariate risk (odds ratio) of one-year mortality according to tertiles of pGSN and All Cause, CVD, and Infectious causes of death at one year.

| Risk for All Cause Death | | Odds Ratio * | 95% CI | P value |
|---|---|---|---|---|
| Tertiles of pGSN | | | | |
| Tertile 1 | ≥150 mg/L | 1.0 | (ref) | |
| Tertile 2 | 130-149 mg/L | 2.1 | 0.7-6.7 | 0.19 |
| Tertile 3 | <130 mg/L | 3.4 | 1.2-9.4 | 0.01 |
| | | | P for Trend = | 0.01 |
| Risk for CVD Deaths | | | | |
| Tertile 1 | ≥150 mg/L | 1.0 | (ref) | |
| Tertile 2 | 130-149 mg/L | 1.4 | 0.3-5.2 | 0.65 |
| Tertile 3 | <130 mg/L | 2.4 | 0.6-8.2 | 0.10 |
| | | | P for Trend = | 0.05 |
| Risk for Infectious Deaths | | | | |
| Tertile 1 | ≥150 mg/L | 1.0 | (ref) | |
| Tertile 2 | 130-149 mg/L | 3.2 | 0.7-15.5 | 0.13 |
| Tertile 3 | <130 mg/L | 5.4 | 1.3-22.5 | 0.03 |
| | | | P for trend = | 0.01 |

* Model adjusted for baseline Age, Gender, Race, BMI, Cause of ESRD, Blood Pressure, Vascular Access, and baseline serum Albumin, Calcium, Phosphorus, Creatinine, WBC, Platelet Count, and hs C-reactive protein.

TABLE 4

Multivariable risk (Odds Ratio) of one-year mortality according to Veno-Venous Catheter status at baseline, and pGSN and actin status.

| | Cases | Controls | Odds Ratio * | 95% CI |
|---|---|---|---|---|
| No Veno-Venous Catheter (n = 93) | | | | |
| +pGSN, −Actin | 4 | 14 | 1.0 | (ref) |
| −pGSN, −Actin | 3 | 8 | 0.3 | 0.1-7.2 |
| +pGSN, +Actin | 5 | 16 | 1.0 | 0.2-7.9 |
| −pGSN, +Actin | 22 | 21 | 2.4 | 0.5-12.1 |
| Veno-Venous Catheter (n = 130) | | | | |
| +pGSN, −Actin | 4 | 12 | 1.0 | (ref) |
| −pGSN, −Actin | 11 | 12 | 3.9 | 0.6-26.4 |
| +pGSN, +Actin | 15 | 14 | 11.1 | 1.8-69.5 |
| −pGSN, +Actin | 50 | 12 | 25.9 | 4.3-157.0 |

* Elevated baseline pGSN (pGSN ≥ 141 mg/L, + pGSN), low baseline pGSN (pGSN < 141 mg/L, −pGSN); No Detectable Actin (−Actin); Detectable Actin (+Actin).

* Model adjusted for baseline Age, Gender, Race, Body Mass Index, Cause of ESRD, Blood Pressure, Vascular Access, and baseline serum Albumin, Calcium, Phosphorus, Creatinine, White Blood Cell Count, Platelet Count, and high sensitivity C-reactive protein.

TABLE 5

Levels of plasma gelsolin (mg/L) in clinical states

| Source | N | Mean (range/SD) | Median | Methodology |
|---|---|---|---|---|
| Normal | | | | |
| Dahl, et al. (1999)[58] | 25 | 207 (151-621) | 200 | Nephelometry |
| DiNubile, et al. (1998)[59] | 11 | 440 ± 150 | | Western blot |
| Ito, et al. (1992)[60] | 43 | 226 ± 52 | 220 | ELISA |
| Smith, et al. (1987)[61] | 56 | 240 ± 50 | 250 | ELISA, nucleation |
| Mounzer, et al. (1999)[18] | 11 | 517 ± 134 | 500 | Western blot |
| Smith, et al, (1988)[62] | | | | |
| Healthy Gambian children | 11 | 367 ± 67 | | Nucleation |
| Convalescent from malaria | 11 | 263 ± 160 | 240 | Nucleation |
| Suhler, et al. (1997)[16] | 25 | 260 ± 20 | | Western blot |
| Acute lung injury | | | | |
| Lind, et al. (1988)[63]† | 20 | 89 ± 33 | 86 | Nucleation |
| Fulminant hepatic necrosis | | | | |
| Suhler, et al. (1997)[16] | 18 | 100 ± 15 | | Western blot |
| Acute hepatitis | | | | |
| Ito, et al. (1992)[60]† | 14 | 80 ± 40 | 80 | ELISA |
| Post-hematopoietic stem call transplantation with death from interstitial pneumonia | | | | |
| DiNubile, et al. (1998)[59] | 9 | 100 ± 50 | | Western blot |
| Acute myocardial infarction | | | | |
| Suhler, et al. (1997)[16] | 10 | 180 ± 20 | | Western blot |
| Rhabdomyolysis | | | | |
| Suhler, et al. (1997)[16] | 12 | 170 ± 20 | | Western blot |
| Löfberg, et al. (1998)[64] | 5 | 116 ± 22 | 100 | RIA |
| Bacterial pneumonia | | | | |
| Smith, et al. (1988)[62] | 8 | 116 ± 89 | | Nucleation |
| Lind, et al. (1988)[63] | 6 | 117 ± 21 | 115 | Nucleation |

TABLE 5-continued

Levels of plasma gelsolin (mg/L) in clinical states

| Source | N | Mean (range/SD) | Median | Methodology |
|---|---|---|---|---|
| Sepsis | | | | |
| Suhler, et al. (1997)[16] | 6 | 130 ± 20 | | |
| Acute falciparum malaria | | | | |
| Smith, et al. (1988)[62] | 18 | 126 ± 45 | | Nucleation |
| Major trauma, surgery, burns | | | | |
| Lee, et al. (2006)[11] | | | | |
| Overall | 31 | 73 | 70 | Nucleation |
| ICU survivors | 28 | 81 (20-181) | | Nucleation |
| ICU non-survivors | 3 | 26 (25-60) | | Nucleation |
| Dahl, et al. (1999)[58] | 23 | 51 (7-967) | 55 | Nephelometry |
| Mounzer, et al. (1999)[18] | 64 | 339 ± 82 | 290 | Western blot |

All values are in mg/L. Unless otherwise noted, effects to detect actin were not performed.
†Actin detected in plasma.
‡Actin not detected in plasma.

REFERENCES

1. U.S. Renal Data System, USRDS 2006 Annual Data Report. Bethesda: National Institutes of Health, National Institute of Diabetes and Digestive and Kidney Diseases; 2006.
2. Foley R N, Parfrey P S, Sarnak M J. Clinical epidemiology of cardiovascular disease in chronic renal disease. Am J Kidney Dis 1998; 32(5 Suppl 3):S112-9.
3. Meyer T W, Hostetter T H. Uremia. N Engl J Med 2007; 357(13):1316-25.
4. Kalantar-Zadeh K, Kopple J D, Block G, Humphreys M H. A malnutrition-inflammation score is correlated with morbidity and mortality in maintenance hemodialysis patients. Am J Kidney Dis 2001; 38(6):1251-63.
5. Zimmermann J, Herrlinger S, Pruy A, Metzger T, Wanner C. Inflammation enhances cardiovascular risk and mortality in hemodialysis patients. Kidney Int 1999; 55(2): 648-58.
6. Zoccali C, Mallamaci F, Tripepi G. Traditional and emerging cardiovascular risk factors in end-stage renal disease. Kidney Int Suppl 2003(85):S105-10.
7. Johansen K L, Young B, Kaysen G A, Chertow G M. Association of body size with outcomes among patients beginning dialysis. Am J Clin Nutr 2004; 80(2):324-32.
8. Fouque D, Kalantar-Zadeh K, Kopple J, et al. A proposed nomenclature and diagnostic criteria for protein-energy wasting in acute and chronic kidney disease. Kidney Int 2007.
9. Christofidou-Solomidou M, Scherpereel A, Solomides C C, et al. Recombinant plasma gelsolin diminishes the acute inflammatory response to hyperoxia in mice. J Investig Med 2002; 50(1):54-60.
10. Lee P S, Waxman A B, Cotich K L, Chung S W, Perrella M A, Stossel T P. Plasma gelsolin is a marker and therapeutic agent in animal sepsis. Crit Care Med 2007; 35(3): 849-55.
11. Lee P S, Drager L R, Stossel T P, Moore F D, Rogers S O. Relationship of plasma gelsolin levels to outcomes in critically ill surgical patients. Annals of surgery 2006; 243(3):399-403.
12. Osborn T M, Dahlgren C, Hartwig J H, Stossel T P. Modifications of cellular responses to lysophosphatidic acid and platelet-activating factor by plasma gelsolin. American journal of physiology 2007; 292(4):C1323-30.
13. Kwiatkowski D J, Stossel T P, Orkin S H, Mote J E, Colten H R, Yin H L. Plasma and cytoplasmic gelsolins are encoded by a single gene and contain a duplicated actin-binding domain. Nature 1986; 323(6087):455-8.
14. Lee W M, Galbraith R M. The extracellular actin-scavenger system and actin toxicity. N Engl J Med 1992; 326(20):1335-41.
15. Kwiatkowski D J. Functions of gelsolin: motility, signaling, apoptosis, cancer. Current opinion in cell biology 1999; 11(1):103-8.
16. Suhler E, Lin W, Yin H L, Lee W M. Decreased plasma gelsolin concentrations in acute liver failure, myocardial infarction, septic shock, and myonecrosis. Crit Care Med 1997; 25(4):594-8.
17. Jordan J R, Moore E E, Damle S S, et al. Gelsolin is depleted in post-shock mesenteric lymph. The Journal of surgical research 2007; 143(1):130-5.
18. Mounzer K C, Moncure M, Smith Y R, Dinubile M J. Relationship of admission plasma gelsolin levels to clinical outcomes in patients after major trauma. Am J Respir Crit Care Med 1999; 160(5 Pt 1):1673-81.
19. Lind S E, Smith D B, Janmey P A, Stossel T P. Role of plasma gelsolin and the vitamin D-binding protein in clearing actin from the circulation. J Clin Invest 1986; 78(3):736-42.
20. Erukhimov J A, Tang Z L, Johnson B A, et al. Actin-containing sera from patients with adult respiratory distress syndrome are toxic to sheep pulmonary endothelial cells. Am J Respir Crit Care Med 2000; 162(1):288-94.
21. Mintzer E, Sargsyan H, Bittman R. Lysophosphatidic acid and lipopolysaccharide bind to the PIP2-binding domain of gelsolin. Biochimica et biophysica acta 2006; 1758(1):85-9.
22. Teng M, Wolf M, Lowrie E, Ofsthun N, Lazarus J M, Thadhani R. Survival of patients undergoing hemodialysis with paricalcitol or calcitriol therapy. N Engl J Med 2003; 349(5):446-56.
23. Teng M, Wolf M, Ofsthun M N, et al. Activated injectable vitamin D and hemodialysis survival: a historical cohort study. J Am Soc Nephrol 2005; 16(4):1115-25.
24. Keltai M, Tonelli M, Mann J F, et al. Renal function and outcomes in acute coronary syndrome: impact of clopidogrel. Eur J Cardiovasc Prev Rehabil 2007; 14(2):312-8.
25. Kouyama T, Mihashi K. Fluorimetry study of N-(1-pyrenyl)iodoacetamide-labelled F-actin. Local structural change of actin protomer both on polymerization and on 25. binding of heavy meromyosin. European journal of biochemistry/FEBS 1981; 114(1):33-8.
26. Wolf M, Shah A, Gutierrez O, et al. Vitamin D levels and early mortality among incident hemodialysis patients. Kidney Int 2007; 72(8):1004-13.
27. Janmey P A, Lind S E, Capacity of human serum to depolymerize actin filaments. Blood 1987; 70(2):524-30.
28. Owen W F, Jr., Lew N L, Liu Y, Lowrie E G, Lazarus J M. The urea reduction ratio and serum albumin concentration as predictors of mortality in patients undergoing hemodialysis. N Engl J Med 1993; 329(14):1001-6.
29. Powe N R, Jaar B, Furth S L, Hermann J, Briggs W. Septicemia in dialysis patients: incidence, risk factors, and prognosis. Kidney Int 1999; 55(3):1081-90.
30. Chauhan V P, Ray I, Chauhan A, Wisniewski H M. Binding of gelsolin, a secretory protein, to amyloid beta-protein. Biochem Biophys Res Commun 1999; 258(2): 241-6.
31. Goetzl E J, Lee H, Azuma T, Stossel T P, Turck C W, Karliner J S. Gelsolin binding and cellular presentation of lysophosphatidic acid. J Biol Chem 2000; 275(19):14573-8.
32. Yamamoto H, Ito H, Nakamura H, et al. Human plasma gelsolin binds adenosine triphosphate. Journal of biochemistry 1990; 108(4):505-6.
33. Lind S E, Janmey P A. Human plasma gelsolin binds to fibronectin. J Biol Chem 1984; 259(21):13262-6.
34. DiNubile M J, Stossel T P, Ljunghusen O C, Ferrara J L, Antin J H. Prognostic implications of declining plasma gelsolin levels after allogeneic stem cell transplantation. Blood 2002; 100(13):4367-71.
35. Rothenbach P A, Dahl B, Schwartz J J, et al. Recombinant plasma gelsolin infusion attenuates burn-induced pulmonary microvascular dysfunction. J Appl Physiol 2004; 96(1):25-31.
36. McIntyre C W, Selby N M, Sigrist M, Pearce L E, Mercer T H, Naish P F. Patients receiving maintenance dialysis have more severe functionally significant skeletal muscle wasting than patients with dialysis-independent chronic kidney disease, Nephrol Dial Transplant 2006; 21(8): 2210-6.
37. Kaysen G A, Greene T, Daugirdas J T, et al. Longitudinal and cross-sectional effects of C-reactive protein, equilibrated normalized protein catabolic rate, and serum bicarbonate on creatinine and albumin levels in dialysis patients. Am J Kidney Dis 2003; 42(6):1200-11.
38. Kalantar-Zadeh K, McAllister C J, Lehn R S, Lee G H, Nissenson A R, Kopple J D. Effect of malnutrition-inflammation complex syndrome on EPO hyporesponsiveness in maintenance hemodialysis patients. Am J Kidney Dis 2003; 42(4):761-73.
39. Besarab A, Bolton W K, Browne X, et al. The effects of normal as compared with low hematocrit values in patients with cardiac disease who are receiving hemodialysis and epoetin. N Engl J Med 1998; 339(9):584-90.
40. Eknoyan G, Beck G J, Cheung A K, et al. Effect of dialysis dose and membrane flux in maintenance hemodialysis. N Engl J Med 2002; 347(25):2010-9.
41. Wanner C, Krane V, Marz W, et al. Atorvastatin in patients with type 2 diabetes mellitus undergoing hemodialysis. N Engl J Med 2005; 353(3):238-48.
42. Weiner D J, Bucki R, Janmey P A. The antimicrobial activity of the cathelicidin LL37 is inhibited by F-actin bundles and restored by gelsolin. American journal of respiratory cell and molecular biology 2003; 28(6):738-45.
43. Mitch W E, Goldberg A L. Mechanisms of muscle wasting. The role of the ubiquitin-proteasome pathway. N Engl J Med 1996; 335(25):1897-905.
44. Ni X G, Zhou L, Wang G Q, et al. The ubiquitin-proteasome pathway mediates gelsolin protein downregulation in pancreatic cancer. Mol Med 2008; 14(9-10):582-9.
45. Beddhu S, Cheung A K, Larive B, et al. Inflammation and inverse associations of body mass index and serum creatinine with mortality in hemodialysis patients. J Ren Nutr 2007; 17(6):372-80.
46. Semba R D, Ricks M O, Ferrucci L, Xue Q L, Guralnik J M, Fried L P. Low serum selenium is associated with anemia among older adults in the United States. Eur J Clin Nutr 2007.
47. Mejean C, Roustan C, Benyamin Y. Anti-actin antibodies. Detection and quantitation of total and skeletal muscle actin in human plasma using a competitive ELISA. Journal of immunological methods 1987; 99(1): 129-35.
48. Himmelfarb J, Stenvinkel P, Ikizler T A, Hakim R M. The elephant in uremia: oxidant stress as a unifying concept of cardiovascular disease in uremia. Kidney Int 2002; 62(5): 1524-38.
49. Mezzano U, Pais E O, Aranda E, et al. Inflammation, not hyperhomocysteinemia, is related to oxidative stress and hemostatic and endothelial dysfunction in uremia. Kidney Int 2001; 60(5):1844-50.
50. Mezzano D, Tagle R, Pais E, et al. Endothelial cell markers in chronic uremia: relationship with hemostatic defects and severity of renal failure. Thromb Res 1997; 88(6):465-72.
51. Jensen T, Bjerre-Knudsen J, Feldt-Rasmussen B, Deckert T. Features of endothelial dysfunction in early diabetic nephropathy. Lancet 1989; 1(8636):461-3.
52. Hsuch W A, Anderson P W. Hypertension, the endothelial cell, and the vascular complications of diabetes mellitus, Hypertension 1992; 20(2):253-63.
53. Lazarus J M, Owen W F. Role of bioincompatibility in dialysis morbidity and mortality. Am J Kidney Dis 1994; 24(6):1019-32.
54. Haddad J G, Harper K D, Guoth M, Pietra G G, Sanger J W. Angiopathic consequences of saturating the plasma scavenger system for actin. Proc Natl Acad Sci USA 1990; 87(4):1381-5.
55. Walker T S, Tomlin K L, Worthen G S, et al. Enhanced *Pseudomonas aeruginosa* biofilm development mediated by human neutrophils. Infection and immunity 2005; 73(6):3693-701.
56. Trautner B W, Darouiche R O. Role of biofilm in catheter-associated urinary tract infection. American journal of infection control 2004; 32(3):177-83.
57. Kalantar-Zadeh K, Kopple J D, Block G, Humphreys M H. A malnutrition-inflammation score is correlated with morbidity and mortality in maintenance hemodialysis patients. Am J Kidney Dis 2001; 38(6):1251-63.
58. Dahl B, Schiodt F V, Ott P, Ovozdenovic R, Yin H L, Lee W M. Plasma gelsolin is reduced in trauma patients. Shock (Augusta, Ga. 1999; 12(2): 102-4.
59. DiNubile M, Antin J, Bressler S, Stossel T, Ferrara J. Decreased gelsolin levels are associated with interstitial pneumonia after allogeneic BMT. Blood 1998; 92(Supplement):683a.
60. Ito H, Kambe H, Kimura Y, et al. Depression of plasma gelsolin level during acute liver injury. Gastroenterology 1992; 102(5):1686-92.

61. Smith D B, Janmey P A, Herbert T J, Lind S E. Quantitative measurement of plasma gelsolin and its incorporation into fibrin clots. J Lab Clin Med 1987; 110(2):189-95.
62. Smith D B, Janmey P A, Sherwood J A, Howard R J, Lind S E. Decreased plasma gelsolin levels in patients with *Plasmodium falciparum* malaria: a consequence of hemolysis? Blood 1988; 72(1):214-8.
63. Lind S E, Smith D B, Janmey P A, Stossel T P. Depression of gelsolin levels and detection of gelsolin-actin complexes in plasma of patients with acute lung injury. The American review of respiratory disease 1988; 138(2):429-34.
64. Lofberg M, Paunio T, Tahtela R, Kiura S, Somer H. Serum gelsolin and rhabdomyolysis. Journal of the neurological sciences 1998; 157(2):187-90.

EQUIVALENTS

The foregoing written specification is considered to be sufficient to enable one ordinarily skilled in the art to practice the invention. The present invention is not to be limited in scope by the example(s) provided, since the example(s) are intended as mere illustrations of one or more aspects of the invention. Other functionally equivalent embodiments are considered within the scope of the invention. Various modifications of the invention in addition to those shown and described herein will become apparent to those skilled in the art from the foregoing description. Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth or illustrated in the drawings. The invention is capable of other embodiments and of being practiced or of being carried out in various ways.

Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

All references, patents and patent applications that are recited in this application are incorporated by reference herein in their entirety.

We claim:

1. A method for evaluating the efficacy of a therapy in a chronic renal failure subject, the method comprising:
   (i) determining a level of plasma gelsolin from the subject,
   (ii) comparing the level of plasma gelsolin from the subject to a predetermined value of about 150 ng of gelsolin/µl of plasma,
   (iii) determining whether the level of plasma gelsolin is at or above the predetermined value, said determination indicating that the therapy is efficacious; and
   (iv) continuing the therapy in the subject having a level of plasma gelsolin at or above the predetermined value, or discontinuing or changing the therapy in the subject having a level of plasma gelsolin below the predetermined value.

2. The method of claim 1, wherein (i) and (ii) are repeated so as to monitor the subject's levels of gelsolin over time.

3. The method of claim 1, wherein the level of plasma gelsolin is in a body fluid of the subject.

4. The method of claim 3, wherein the body fluid is blood, plasma, serum, cerebrospinal fluid (CSF), or urine.

5. The method of claim 1, wherein the subject is on dialysis.

6. The method of claim 1, wherein the subject has end-stage renal disease.

7. The method of claim 1, wherein the therapy is to reduce the risk of infection.

8. The method of claim 7, wherein the infection is caused by a gram-positive bacterium, a gram-negative bacterium, an acid-fast bacillus, a spirochete, an actinomycete, a virus, a fungus, a parasite, a *Ureoplasma* species, a *Mycoplasma* species, a *Chlamydia* species, or a *Pneumocystis* species.

9. The method of claim 8, wherein the gram-positive bacterium is a *Pasteurella* species, a *Staphylococcus* species, a *Streptococcus* species, a *Bacillus anthracis*, a *Corynebacterium* species, a *Diphtheroids* species, a *Listeria* species, a *Erysipelothrix* species, or a *Clostridium* species.

10. The method of claim 8, wherein the gram-negative bacterium is a *Neisseria* species, a *Branhamella* species, an *Escherichia* species, an *Enterobacter* species, a *Proteus* species, a *Pseudomonas* species, a *Klebsiella* species, a *Salmonella* species, a *Shigella* species, a *Serratia* species, an *Acinetobacter* species, a *Haemophilus* species, a *Brucella* species, a *Yersinia* species, a *Francisella* species, a *Pasteurella* species, a *Vibrio cholera* species, a *Flavobacterium* species, a *Pseudomonas* species, a *Campylobacter* species, a *Bacteroides* species, a *Fusobacterium* species, a *Calymmatobacterium* species, a *Streptobacillus* species, or a *Legionella* species.

11. A method for characterizing a chronic renal failure subject's mortality risk, the method comprising:
   determining a level of plasma gelsolin obtained from the subject,
   comparing the level of plasma gelsolin obtained from the subject to a predetermined value of about 150 ng of gelsolin/µl of plasma,
   characterizing the subject's mortality risk as increased if the level of plasma gelsolin is below about 150 ng of gelsolin/µl of plasma, relative to a subject with a level of plasma gelsolin above about 150 ng of gelsolin/µl of plasma; and
   administering to the subject gelsolin in an amount effective to raise the level of plasma gelsolin in the subject above about 150 ng of gelsolin/µl of plasma.

12. The method of claim 11, wherein the level of plasma gelsolin is in a body fluid of the subject.

13. The method of claim 11, wherein the mortality is caused by an infection.

14. The method of claim 11, wherein the mortality is caused by a cardiovascular event.

15. The method if claim 11, wherein the subject is on dialysis.

16. The method of claim 11, wherein the subject has end-stage renal disease.

* * * * *

UNITED STATES PATENT AND TRADEMARK OFFICE
CERTIFICATE OF CORRECTION

PATENT NO. : 9,575,072 B2  
APPLICATION NO. : 12/358868  
DATED : February 21, 2017  
INVENTOR(S) : Ravi Thadhani et al.

It is certified that error appears in the above-identified patent and that said Letters Patent is hereby corrected as shown below:

In the Claims

At Column 38, Claim 15, Line 58, "method if claim 11" should read --method of claim 11--

Signed and Sealed this
Seventeenth Day of April, 2018

Andrei Iancu
*Director of the United States Patent and Trademark Office*